United States Patent
Loftsson et al.

(10) Patent No.: US 12,090,161 B2
(45) Date of Patent: Sep. 17, 2024

(54) TREATMENT OF OCULAR INFLAMMATION

(71) Applicant: Oculis Operations Sàrl, Lausanne (CH)

(72) Inventors: Thorsteinn Loftsson, Reykjavik (IS); Zoltan Fulop, Budapest (HU)

(73) Assignee: Oculis Operations Sàrl, Lausanne (CH)

(*) Notice: Subject to any disclaimer, the term of this patent is extended or adjusted under 35 U.S.C. 154(b) by 0 days.

(21) Appl. No.: 18/383,993

(22) Filed: Oct. 26, 2023

(65) Prior Publication Data
US 2024/0058360 A1 Feb. 22, 2024

Related U.S. Application Data

(63) Continuation of application No. 17/624,311, filed as application No. PCT/EP2020/068398 on Jun. 30, 2020.

(30) Foreign Application Priority Data

Jul. 1, 2019 (EP) .................................... 19183719
May 12, 2020 (EP) .................................... 20174202

(51) Int. Cl.

| A61K 31/573 | (2006.01) |
|---|---|
| A61K 9/00 | (2006.01) |
| A61K 47/02 | (2006.01) |
| A61K 47/10 | (2017.01) |
| A61K 47/12 | (2006.01) |
| A61K 47/14 | (2017.01) |
| A61K 47/20 | (2006.01) |
| A61K 47/40 | (2006.01) |
| A61P 27/02 | (2006.01) |
| A61P 29/00 | (2006.01) |

(52) U.S. Cl.
CPC .......... *A61K 31/573* (2013.01); *A61K 9/0048* (2013.01); *A61K 47/02* (2013.01); *A61K 47/10* (2013.01); *A61K 47/12* (2013.01); *A61K 47/14* (2013.01); *A61K 47/20* (2013.01); *A61K 47/40* (2013.01); *A61P 27/02* (2018.01); *A61P 29/00* (2018.01)

(58) Field of Classification Search
CPC .... A61K 31/573; A61K 9/0048; A61K 47/02; A61K 47/10; A61K 47/12; A61K 47/14; A61K 47/20; A61K 47/40; A61P 27/02; A61P 29/00
See application file for complete search history.

(56) References Cited

U.S. PATENT DOCUMENTS

| 5,051,402 A | 9/1991 | Kurihara et al. |
|---|---|---|
| 5,472,954 A | 12/1995 | Loftsson et al. |
| 5,951,971 A | 9/1999 | Kawashima et al. |
| 7,893,040 B2 | 2/2011 | Loftsson et al. |
| 8,633,172 B2 | 1/2014 | Loftsson et al. |
| 8,999,953 B2 | 4/2015 | Loftsson et al. |
| 10,159,746 B2 | 12/2018 | Lewis et al. |
| 11,135,311 B2 | 10/2021 | Loftsson et al. |
| 11,491,240 B2 | 11/2022 | Loftsson et al. |
| 2002/0045601 A1 | 4/2002 | Kawashima et al. |
| 2002/0064524 A1 | 5/2002 | Cevc |
| 2002/0198174 A1 | 12/2002 | Lyons |
| 2003/0059470 A1 | 3/2003 | Muller |
| 2004/0077562 A1 | 4/2004 | Chandavarkar |
| 2005/0031697 A1 | 2/2005 | Vehige et al. |
| 2005/0234018 A1 | 10/2005 | Lyons et al. |
| 2007/0020336 A1 | 1/2007 | Loftsson et al. |
| 2007/0148192 A1 | 6/2007 | Laddha |
| 2008/0119448 A1 | 5/2008 | Friedlaender et al. |
| 2008/0145430 A1 | 6/2008 | Panmai et al. |
| 2009/0312724 A1 | 12/2009 | Pipkin et al. |
| 2013/0296446 A1 | 11/2013 | Furumiya et al. |
| 2014/0057854 A1 | 2/2014 | Mitra |
| 2014/0163080 A1 | 6/2014 | Horn |
| 2015/0071971 A1 | 3/2015 | Amancha et al. |

(Continued)

FOREIGN PATENT DOCUMENTS

| CN | 1559413 A | 1/2005 |
|---|---|---|
| CN | 1785192 A | 6/2006 |

(Continued)

OTHER PUBLICATIONS

Loftsson et al. ("Cyclodextrins in eye drop formulations: enhanced topical delivery of corticosteroids to the eye", Acta Ophthalmol Scand. Apr. 2002;80(2):144-50) (Year: 2002).*
US, 2024/0058358 A1, U.S. Appl. No. 18/383,987, Loftsson et al., Feb. 22, 2024.
US, 2024/0058359 A1, U.S. Appl. No. 18/383,991, Loftsson et al., Feb. 22, 2024.
US, 2024/0058361 A1, U.S. Appl. No. 18/383,999, Loftsson et al., Feb. 22, 2024.
US, 2024/0058362 A1, U.S. Appl. No. 18/384,000, Loftsson et al., Feb. 22, 2024.
Gudmundsdottir, B.S. et al. γ-Cyclodextrin nanoparticle eye drops with dorzolamide: effect on intraocular pressure in man. J Ocul Pharmacol Ther. 30:35-41(2014).
US, 2024/0091377 A1, U.S. Appl. No. 18/517,529, Loftsson et al., Mar. 21, 2024.

(Continued)

*Primary Examiner* — Robert A Wax
*Assistant Examiner* — Quanglong N Truong
(74) *Attorney, Agent, or Firm* — Knowles Intellectual Property Strategies, LLC

(57) ABSTRACT

The present disclosure relates to a method for stabilizing the pH of an aqueous composition comprising a drug which is prone to oxidation, said method comprising the addition of an additive to prevent oxidation of the drug which is prone to oxidation. In particular, the present disclosure relates to a method for stabilizing the pH of an aqueous composition comprising a corticosteroid, said method comprising the addition of an additive to prevent oxidation of the corticosteroid. The present disclosure also relates to a composition comprising a corticosteroid and an additive to prevent oxidation of the corticosteroid.

26 Claims, No Drawings

(56) References Cited

U.S. PATENT DOCUMENTS

| | | | |
|---|---|---|---|
| 2015/0111838 A1 | 4/2015 | Lewis et al. | |
| 2016/0346347 A1 | 12/2016 | Loftsson | |
| 2018/0147214 A1 | 5/2018 | Ostrow et al. | |
| 2018/0147297 A1* | 5/2018 | Loftsson | A61K 9/50 |
| 2019/0070198 A1 | 3/2019 | El-Shabrawi | |
| 2019/0105264 A1 | 4/2019 | Higuchi et al. | |
| 2019/0231782 A1 | 8/2019 | Chen et al. | |

FOREIGN PATENT DOCUMENTS

| | | |
|---|---|---|
| CN | 101926760 A | 12/2010 |
| CN | 115837027 A | 3/2023 |
| EP | 0579435 B1 | 1/1994 |
| EP | 0709099 A2 | 5/1996 |
| EP | 1047406 B1 | 4/2003 |
| KR | 20140026953 A | 3/2014 |
| WO | WO 1999/36055 A1 | 7/1999 |
| WO | WO 2004/069280 A1 | 8/2004 |
| WO | WO 2004/087100 A1 | 10/2004 |
| WO | WO 2005/105067 A2 | 11/2005 |
| WO | WO 2009/129155 A2 | 10/2009 |
| WO | WO 2017/083799 A1 | 5/2017 |
| WO | WO 201/196881 A1 | 11/2017 |
| WO | WO 2018/100434 A1 | 6/2018 |
| WO | WO 2020/139525 A1 | 7/2020 |
| WO | WO 2021/001366 A1 | 1/2021 |

OTHER PUBLICATIONS 2.9.31 Particle size analysis by laser light diffraction, European Pharmacopeia 9.0, pp. 349-352.
Ammar et al. "Cyclodextrins in acetazolamide eye drop formulations" Pharmazie, vol. 53, pp. 559-562, Govi-Verlag Pharmazeutischer Verkag GmbH, 1998, Eschborn, Germany.
Beeley et al. Fabrication, implantation, elution, and retrieval of a steroid-loaded polycaprolactone subretinal implant Journal of biomedical materials research, vol. 74, pp. 437-444, Wiley Periodicals, Inc., USA, 2005.
Bhatia, Saurabh, "Chapter 2: Nanparticles Types, classification, characterization, fabrication methods and drug delivery applications" Natural Polymer Drug Delivery Systems, pp. 33-93, 2016.
Bonini, M. et al. Self-assembly of beta-cyclodextrin in water. Part 1: Cryo-TEM and dynamic and static light scattering. Langmuir 22, pp. 1478-1484, 2006.
Brewster, Marcus E. et al. "Cycolodextrins as pharmaceutical solubilizers", Advanced Drug Delivery Reviews, vol. 59, pp. 645-666 (2007).
Chadha, Renu et al. "Kinetics of degradation of diclofenac sodium in aqueous solution determined by a calorimetric method," Die Pharmazie, vol. 58, pp. 631-635 (2003).
Chen, Bin et al. "A comparative study of enol aldehyde formation from betamethasone, dexamethasone, beclomethasone and related compounds under acidic and alkaline conditions" Steroids, vol. 74, No. 1, pp. 30-41, 2009.
Chen, Quan et al. "A validated, stability-indicating HPLC method for the determination of dexamethasone related substances on dexamethasone-coated drug-eluting stents" Journal of Pharmaceutical and Biomedical Analysis, 48, 732-738, 2008.
Cohen, E.M. "Dexamethasone, Analytical Profiles of Drug Substances," vol. 2, pp. 163-197 (1973).
Conrow, Raymond E. et al. "Corticosteroid Decomposition via a Mixed Anhydride", The Journal of Organic Chemistry, vol. 67, pp. 6835-3836 (2002).
Dalton, K. et al. Physical Properties of soft contact lens solutions, Optometry and Vision Science, vol. 85m No. 2, pp. 122-128, Feb. 2008.
Dalton, PH "Osmolality and viscosity of artificial tears" American Academy of Optometry, downloaded from <URL https://www.aaopt.org/detail/kowledge-base-article/ph-osmolality-and-viscosity-artificial-tears> on Sep. 24, 2021, 2 pages, 2008.

Duan et al. "Cyclodextrin solubilization of the antibacterial agents triclosan and tricloscarban; formation of aggregates and higher-order complexes" International Journal of Pharmaceutics, vol. 297, pp. 213-222, 2005, Netherlands.
Fenyvesi, E., "Approved Pharmaceutical Products Continuing Cyclodextrins," Cyclodextrin News, vol. 27, No. 2, Feb. 2013.
Frioriksdottir, Hafru "Polymer enhancement of cyclodextrin complexation in vivo and in vitro observations," A Doctoral Thesis, 1997, pp. 6-117, University, IS.
Gan, L. et al. "Recent advances in topical ophthalmic drug delivery with lipid-based nanocarriers" Drug Discov. Today, vol. 18, pp. 290-297, 2013.
Gonzalez-Gaitano et al., "The aggregation of cyclodextrins as studied by Photon Correction Spectroscopy" Journal of Inclusion Phenomena and Macrocylclic Chemistry, vol. 44, pp. 101-105, Kluwer Academic Publishers, Netherlands, 2002.
He, Y. et al. "Cyclodextrin-based aggregates and characterization by microscopy" Micron, vol. 39, pp. 495-516, 2008.
Hidaka, Teturo, et al. "Studies on betamethasone: Behavior of betamethasone in acid or alkaline medium, Photolysis and Oxidation" Yakugaku Zasshi, vol. 100, No. 1, pp. 72-80 (1980).
Higuchi, T. et al. "Phase solubility techniques. Advances in Analytical Chemistry of Instrumentation" vol. 4, pp. 117-212, 1965.
Horsky, J. et al. "Inclusion complexes of proteins: interaction of cyclodextrins with peptides containing aromatic amino acids studies by competitive spectrophotometry" J. Inclusion Phenom. Mal. Recognit, Chem., vol. 18, pp. 291-300, 1994.
International Search Report and Written Opinion for PCT/EP2020/068398, dated Aug. 17, 2020, 10 pages.
International Search Report and Written Opinion for PCT/IB20417/001659, dated May 3, 2018, 10 pages.
Jansook, Phatsawee et al. "γCD/HPγCD mixtures as solubilizer: solid-state characterization and sample dexamethasone eye droop suspension" Journal of Pharmacy & Pharmaceutical Sciences, vol. 13, No. 3, pp. 336-350, 2010.
Jansook, Phatsawee, et al. "Effect of self-aggregation of γ-cyclodextrin on drug solubilization" Journal of Inclusion Phenomena and Macrocyclic Chemistry, vol. 68, pp. 229-236, 2010.
Jansook, P. et al."Cyclodextrin-poloxamer aggregates as nanocarriers in eye drop formulations: dexamethasone and amphotericin B" Taylor & Francis, 2016.
Johannessen, G. et al. "Kinetics of y-cyclodextrin nanoparticle suspension eye drops in tear fluid. Acta Ophthalmologica" vol. 92, pp. 550-556, 2014.
Johannsdoltir, S. et al. "Formulations and toxicologic in vivo studies of aqueous cyclosporin an eye drops with cyclodextrin nanoparticles" In J. Pharm. vol. 529, pp. 486-490, 2017.
Johannsdoltir S. et al. "Development of a cyclodextrin-based aqueous cyclosporin a eye drop formulations" Int. J. Pharm. vol. 493, pp. 86-95, 2015.
Jonas, "Intravitreal triamcinolone acetonide for treatment of intraocular oedematous and neovascular diseases" Acta Ophmalogica Scandinavia, vol. 83, 99. 645-663, Munksgaard, Denmark, 2005.
Jozwiakowski, M. et al. "Aqueous solubility behavior of three cyclodexteins" Carbohydrate Research, vol. 143, pp. 51-59, 1985.
Kabat et al. "Not all tears are created equal", Review of Optometry, vol. 142(1), 3 pages, 2005.
Kanai, A. et al. "The effect on the cornea of alpha cyclodextrin vehicle for cyclosporin eye drops" Transplant Proc., vol. 21, pp. 3150-3152, 1989.
Korenfeld et al., OCS-01 (Novel Topical Dexamethasone Formulation) in Inflammation and Pain Post Cataract Surgery: A Randomized, Double-Masked, Vehicle-Controlled Study, Clinical Therapeutics, vol. 44, Issue 12, 2022, pp. 1577-1587.
Kristinsson et al. "Dexamethasone-Cyclodextrin-Polymer Co-complexes in aqueous eye drops" Investigative ophthalmology & Visual science, vol. 37, No. 6 pp. 1199-1203, Lippincott-Raven Publication USA, 1996.
Kunert, K.S. et al. "Goblet cell Nos. and epithelial proliferation in the conjunctiva of patients with dry eye syndrome treated with cyclosporine" Archives of Ophthalmology, vol. 120, pp. 330-337, 2002.

(56) References Cited

OTHER PUBLICATIONS

Kurkov, S.V. et al. "Cyclodextrins", Int. J. Pharm. Vol. 453, pp. 167-180, 2013.

Laupacis, A. et al. "Cyclosporin A: a powerful immunosuppressant" Canadian Medical Association Journal, vol. 126, pp. 1041-1046, 1982.

Lawen, A. "Biosynthesis of cyclosphorins and other natural peptidyl proyl cis/trans isomerase inhibitors" Biochimica et Biophysica Acta, vol. 1850, pp. 2111-2120, 2015.

Le Bourlais, C. et al. "Ophthalmic drug delivery systems-recent advances. Progress in Retinal and Eye Research" vol. 17, pp. 33-58, 1998.

Li, Min Various Types and Mechanisms of Degradation Reactions, Chapter 4, RSC Drug Discovery Series No. 29, Organic Chemistry of Drug Degradation, 2012.

Loftsson et al., "Cyclodextrins and topical drug delivery to the anterior and posterior segments of the eye" International Journal of Pharmaceutics, 2017.

Loftsson et al. "Pharmaceutical applications of cyclodextrins: basic science and product development" Journal of Pharmacy and Pharmacology, vol. 62, pp. 1607-1621, 2010.

Loftsson et al., "Cyclodextrins in eye drop formulations: enhanced topical delivery of corticosteroids to the eye" Acta Ophthalmologica Scandinavia, vol. 80, pp. 144-150, Munksgaard, Denmark, 2002.

Loftsson, T. "Self-assembled cyclodextrin nanoparticles and drug delivery" J. Incl. Phenom. Macro. vol. 80, pp. 1-7, 2014.

Loftsson et al. "Pharmaceutical applications of cyclodextrins: effects on drug permeation through biological membranes" J. Pharm. Pharmacol. 63, pp. 1119-1135, 2011.

Loftsson et al. "Determination of aqueous solubility by heating and equilibration: A technical note" AAPS PharmSciTech 7, article No. 4, 2006.

Loftsson et al. "Topical drug delivery to the posterior segment of the eye: anatomical and physiological considerations" Pharmazie, vol. 63, pp. 171-179, 2008.

Loftsson et al. "Cyclodextrins in drug delivery" Expert Opinion, vol. 2, Drug Delivery, pp. 335-351, Ashley Publications Ltd. London, 2005.

Loftsson et al. "Cyclodextrins in ophthalmic drug delivery" Advanced Drug Delivery Reviews, vol. 36, pp. 59-79, 1999, Netherlands.

Loftsson, et al. "Topical dexamethasone delivery to the retina: An aqueous cyclodextrin-based microsuspension" Journal of drug delivery science and technology, 81, 2023.

Loftsson et al. "The effects of organic salts on the cyclodextrins solubilization of drugs" International Journal of Pharmaceutics, vol. 262, pp. 101-107, 2003, Netherlands.

Loftsson et al. "The effects of water-soluble polymers on cyclodextrins and cyclodextrin solubilization of drugs" J. Drug Del. Sci. Tech. vol. 14, pp. 35-43, 2004 Ed. De Sante France.

Loftsson et al. "Topical drug delivery to the eye: dorzolamide" Acta Ophthalmologica vol. 90, pp. 603-608, 2012.

Loftsson et al. "Self-Association of Cyclodextrins and Cyclodextrin Complexes", Journal of Pharmaceutical Sciences, vol. 93, No. 5, pp. 1091-1099, Wiley-Liss, Inc. and the American Pharmacists Association, USA, 2004.

Loftsson et al. "Cyclodextrins solubilization of the antibacterial agents Triclosan and Triclocarban; Effect of ionization and polymers" Journal of inclusion phenomena and macrocyclic chemistry, vol. 52, pp. 109-117, 2005 Netherlands.

Loftsson et al. "Pharmaceutical applications of cyclodextrins. 1 Drug solubilization and stabilization" Journal of Pharmaceutical Sciences, vol. 85, pp. 1017-1025, 1996.

Loftsson et al. "Evaluation of cyclodextrin solubilization of drugs" International Journal of Pharmaceutics, vol. 302, pp. 18-28, 2005 Netherlands.

Loftsson et al. "Topically effective ocular hypotensive acetazolamide and ethoxyzolamide formulations in rabbits" J. Pharm. Pharmacol. Vol. 46, pp. 503-504, Pharmaceutical Press England, 1994.

Loftsson et al. Cyclodextrin Microparticles for drug delivery to the posterior segment of the eye: Aqueous dexamethasone Eye Drops, vol. 59, No. 5 J. Pharm. Pharmacol. 629-635, 2007.

Loftsson et al. "Cyclodextrin solubilization of benzodiazephines: formulation of midazolam nasal spray" International Journal of Pharmaceutics, vol. 212, pp. 29-40, 2001, Netherlands.

Loftsson et al. "Aqueous eye drops containing drug/cyclodextrin nanoparticles deliver therapeutic drug concentrations to both anterior and posterior segment" Acta Ophthalmologica, 2022.

Magnusdottir et al., "Self-association and cyclodextrin solubilizations of NSAIDs" Journal of Inclusion phenomena and macrocyclic chemistry, vol. 44, pp. 213-218,, Kluwer Academic Publishers, The Netherlands, 2002.

Mele et al., "Non-covalent associations of cyclomaltooligosaccharides (cyclodextrins) with trans-B-carotene in water: evidence for the formation of large aggregates by light scattering and NMR spectroscopy", Carbohydrate Research, vol. 310, 559, pp. 261-267, 1998 Netherland.

Messner, M. et al. "Self-assembled cyclodextrin aggregates and nanoparticles" Int. J. Pharm. vol. 387, pp. 199-208, 2010.

Miyake, K. et al. Enhanced absorption of cyclosporin A by complexation with dimethyl-beta-cyclodextrin in bile duct-cannulated and -noncannulated rats: Biological & Pharmaceutical Bulletin, vol. 22, pp. 66-72, 1999.

Moya-Ortega et al. "Dexamethasone eye drops containing γ-cyclodextrin-based nanogels" Int J. Pharm. 441, 507-515, 2013.

Muankaew, C. et al. "Cyclodextrin-based telmisartan Ophthalmic Suspension: Formulation development for water-insoluble drugs" International Journal of Pharmaceutics, vol. 507, pp. 21-31, 2016.

Muankaew, C. et al. "Effect of γ-cyclodextrin on solubilization and complexion of irbesartan: influence of pH and excipients" Int. J. Pharm. vol. 474, pp. 80-90, 2014.

Myles et al. "Recent progress in ocular drug delivery for posterior segment disease: Emphasis on transscleral iontophoresis" Advanced drug delivery reviews, vol. 57, pp. 2063-2079, 2005, Netherlands.

Oculis Holding AG—Form F-4 Registration Statement; Securities and Exchange Commission; Registration No. 333, filed Nov. 7, 2022.

Oculis announces positive top line results from Diamond Stage 1 Phase 3 Trial in Diabetic Macular Edema with OCS-01 Eye Drops, May 22, 2023.

Oculis Completes Series A Financing, Internet website https://www.businesswire.com/news/home/20160816005055/en/Oculi ...; accessed Aug. 1, 2023, Reykjavik, Iceland, Aug. 16, 2016.

Ohira, Akihiro et al. "Topical dexamethasone ε-cyclodextrin nanoparticle eye drops increase visual acuity and decrease macular thickness in diabetic macular oedema" Acta Ophthalmologica, 93:610-615; 2015.

Peel, M. et al. "Semi-synthesis of cyclosphorins" Biochimica et Biophysica Acta, vol. 1850, pp. 2121-2144, 2015.

Raghava et al. "Periocular routes for retinal drug delivery", Expert Opinion, Drug Delivery, vol. 1 pp. 99-114, Ashley Publications Ltd. 2004, England.

Rowe, Raymond C., et al. "Cyclodextrins", Handbook of Pharmaceutical Excipients, 4th Edition, pp. 186-190, The Pharmaceutical, 2003, London England.

Russo, S. et al. Dexamethasone-netilmicin: a new ophthalmic steroid-antibiotic combination. Effcacy and safety after cataract surgery, Eye (2007) 21, 58-64.

Sabadini, E. et al. "Solubility of cyclomaltooligosaccharides (cyclodextrins) in H2O and D2O: a comparative study" Carbohydrate Research vol. 341, No. 2, pp. 207-274, 2006.

Salminen et al. "Disposition of ophthalmic timolol in treated and untreated rabbit eyes. A multiple and single dose study" Exp. Eye Res. vol. 38, pp. 203-206, Academic Press Inc. London, 1984.

Schloesser, Paul "Oculis eye drop secures another late-stage win, this time in post-cataract surgery inflammation and pain" Endpoint News https://endpts.com/oculis-eye-drop-meets-primary-endpoints-in-phiii-post-surgery-inflammation-and-pain-trial/ Internet accessed Aug. 8, 2023.

Shah, Tirth J et al. "Intracameral dexamethasone injection in the treatment of cataract surgery induced inflammation: design, development, and place in therapy" Clinical Ophthalmology, 12; 2223-2235; 2018.

(56) References Cited

OTHER PUBLICATIONS

Spangler, M. et al. "A validated, stability-indicating method for the assay of dexamethasone in drug substance and drug product analyses, and the assay of preservatives in drug product", Chromatographia, vol. 54, pp. 329-334, 2001.

Stamm, Hermann: Overview of the methods and techniques of measurement of nanoparticles Nanotrust-Possible Health Effects of Manufactured Nanomaterials, 52 pages, 2009.

Stefansson, Einar et al. Topical treatment of diabetic macular edema using dexamethasone ophthalmic suspension: A randomized, double-masked, vehicle-controlled study, Acta Ophthalmologica, 101:22-33; 2023.

Stella, V.J. et al. Cyclodextrins Tox. Pathol. vol. 36, pp. 30-42, 2008.

Sugrue, M.F. "The pharmacology of antiglaucoma drugs", Pharmacology & Therapeutics, vol. 43, pp. 91-138, 1989.

Tanito, M. et al. "Topical dexamethasone-cyclodextrin microparticle eye drops for diabetic macular edema" Invest. Ophth. Vis. Sci. vol. 52, pp. 7944-7948, 2011.

Tayar, El et al. Solvent-dependent conformation and hydrogen-bonding capacity of cyclosphorin A: evidence from partition coefficients and molecular dynamics simulations, J. Med. Chem. vol. 36, pp. 3753-3764, 1993.

Urtti, A. "Challenges and obstacles of ocular pharmacokinetics and drug delivery" Drug Del. Rev., vol. 58, pp. 1131-1135, 2006.

Usayapant A. et al. "Effect of 2-Hydroxypropyl-β-cyclodextrin on the Ocular Absorption of dexamethasone and dexamethasone acetate," Pharmaceutical Research, vol. 8, No. 12, pp. 1495-1499, 1991.

Utine, C.A. et al. Topical Ophthalmic use of cyclosporin A. Ocular Immunology & Inflammation: vol. 18, pp. 352-361, 2010.

Yasukawa et al. "Intracular sustained drug delivery using implantable polymeric devices" Advanced drug delivery reviews, vol. 57, pp. 2033-2046, 2005 Netherlands.

Zimmer et al. "Microspheres and nanoparticles used in ocular delivery systems" Advanced Drug Delivery Reviews, vol. 16.pp. 61-73, 1995 Netherlands.

U.S. Pat. No. 7,893,040 B2, U.S. Appl. No. 11/489,466, Loftsson et al., filed Feb. 22, 2011.

U.S. Pat. No. 8,633,172 B2, U.S. Appl. No. 13/758,955, Loftsson et al., filed Jan. 21, 2014.

U.S. Pat. No. 8,999,953 B2, U.S. Appl. No. 14/106,265, Loftsson et al., filed Apr. 7, 2015.

U.S. Pat. No. 11,135,311 B2, U.S. Appl. No. 15/826,247, Loftsson et al., filed Oct. 5, 2021.

U.S. Pat. No. 11,491,240 A1, U.S. Appl. No. 17/487,354, Loftsson et al., filed Nov. 8, 2022.

US, 2023/0037486 A1, U.S. Appl. No. 17/955,064, Loftsson et al., filed Feb. 9, 2023.

US, 2023/0042785 A1, U.S. Appl. No. 17/973,749, Loftsson et al., filed Feb. 9, 2023.

US, 2022/0354869 A1, U.S. Appl. No. 17/624,311, Loftsson et al., filed Nov. 10, 2022.

U.S. Appl. No. 18/383,987, Loftsson et al., filed Oct. 26, 2023

U.S. Appl. No. 18/383,991, Loftsson et al., filed Oct. 26, 2023

U.S. Appl. No. 18/384,000, Loftsson et al., filed Oct. 26, 2023

U.S. Appl. No. 18/383,999, Loftsson et al., filed Oct. 26, 2023

U.S. Appl. No. 18/517,529, Loftsson et al., filed Nov. 22, 2023.

* cited by examiner

TREATMENT OF OCULAR INFLAMMATION

CROSS-REFERENCE TO RELATED APPLICATIONS

This application is a continuation of U.S. patent application Ser. No. 17/624,311, filed on Dec. 31, 2021; which is a § 371 national stage application based on Patent Cooperation Treaty Application serial number PCT/EP2020/068398, filed Jun. 30, 2020; which claims the benefit of priority to European Patent Application No. 20174202.0, filed May 12, 2020; and European Patent Application No. 19183719.4, filed Jul. 1, 2019 The entirety of each of these applications is incorporated herein for all purposes.

TECHNICAL FIELD

The present disclosure relates to a method for stabilizing the pH of an aqueous composition comprising a drug, said method comprising the addition of an additive to prevent oxidation of the drug. In particular, the present disclosure relates to a method for stabilizing the pH of an aqueous composition comprising a corticosteroid, said method comprising the addition of an additive to prevent oxidation of the corticosteroid. The present disclosure also relates to a composition comprising a corticosteroid and an additive to prevent oxidation of the corticosteroid.

BACKGROUND

Ocular conditions are a worldwide problem: approximately 285 million people worldwide are estimated to be visually impaired. In the US, 2.1 million Americans are diagnosed with age-related macular degeneration (AMD), 2.7 million Americans are diagnosed with glaucoma, 7.7 million Americans are diagnosed with diabetic retinopathy, and 24 million Americans are diagnosed with cataracts.

Most ocular conditions can be treated and/or managed to reduce negative effects, including total blindness. However, current treatments for ocular conditions are limited by the difficulty in delivering effective doses of drugs to target tissues in the eye. In current treatments, topical administration of eye drops is the preferred means of drug administration to the eye due to the convenience and safety of eye drops in comparison to other routes of ophthalmic drug administration such as intravitreal injections and implants (Le Souriais, C., Acar, L., Zia, H., Sado, P. A., Needham, T., Leverge, R., 1998. Ophthalmic drug delivery systems-Recent advances. Progress in Retinal and Eye Research 17, 33-58). Drugs are mainly transported by passive diffusion from the eye surface into the eye and surrounding tissues where, according to Fick's law, the drug is driven into the eye by the gradient of dissolved drug molecules. The passive drug diffusion into the eye is hampered by three major obstacles (Gan, L., Wang, J., Jiang, M., Bartlett, H., Ouyang, D., Eperjesi, F., Liu, J., Gan, Y., 2013. Recent advances in topical ophthalmic drug delivery with lipid-based nanocarriers. Drug Discov. Today 18, 290-297; Loftsson, T., Sigurdsson, H. H., Konradsdottir, F., Gisladottir, S., Jansook, P., Stefansson, E., 2008. Topical drug delivery to the posterior segment of the eye: anatomical and physiological considerations. Pharmazie 63, 171-179; Urtti, A, 2006. Challenges and obstacles of ocular pharmacokinetics and drug delivery. Adv. Drug Del. Rev. 58, 1131-1135).

Recently, applicants have described preparation and testing of cyclodextrin-based eye drops containing dexamethasone (WO2018/100434, Johannesson, G., Moya-Ortega, M. D., Asgrimsdottir, G. M., Lund, S. H., Thorsteinsdottir, M., Loftsson, T., Stefansson, E., 2014. Kinetics of y-cyclodextrin nanoparticle suspension eye drops in tear fluid. Acta Ophthalmologica 92, 550-556; Thorsteinn Loftsson and Einar Stefansson, Cyclodextrin nanotechnology for ophthalmic drug delivery, U.S. Pat. No. 7,893,040 (Feb. 22, 2011); Thorsteinn Loftsson and Einar Stefansson, Cyclodextrin nanotechnology for ophthalmic drug delivery, U.S. Pat. No. 8,633,172 (Jan. 21, 2014); Thorsteinn Loftsson and Einar Stefansson, Cyclodextrin nanotechnology for ophthalmic drug delivery U.S. Pat. No. 8,999,953 (Apr. 7, 2015)).

These studies show that cyclodextrin-based eye drops containing active principle ingredient are promising for the treatment of ocular conditions.

However, under some storage conditions, for example when stored in low-density polyethylene (LDPE) vials for several months, the pH of cyclodextrin-based eye drops with active principle ingredient is not stable and decreases overtime. Thus, it is desirable to develop a method for stabilizing the pH of these aqueous compositions, in order to prevent the pH drop.

BRIEF DESCRIPTION

A first object of the present disclosure is a method for stabilizing the pH of an aqueous composition comprising a drug, said method comprising the addition of an additive to prevent oxidation of the drug.

The inventors have surprisingly found that the addition of an additive to prevent oxidation of the drug to the aqueous solution can prevent the drop of pH, especially during long storage periods.

A second object of the present disclosure is an aqueous composition comprising a corticosteroid, cyclodextrin and an additive to prevent oxidation of the corticosteroid, wherein said additive is present in the composition at a concentration between 0.15% (w/v) and 0.6% (w/v), for example between 0.15% (w/v) and 0.45% (w/v), and preferably at a concentration between 0.2% (w/v) and 0.4% (w/v).

A third object of the present disclosure is the use of an additive to prevent oxidation of a corticosteroid for stabilizing the pH of an aqueous composition comprising a corticosteroid.

A fourth object of the present disclosure is a method for stabilizing the pH of an aqueous composition comprising a drug, said method comprising the use of an oxygen absorber to prevent oxidation of the drug.

DETAILED DESCRIPTION

Definitions

As used herein the term "% by weight of a compound X based on the volume of the composition", also abbreviated as "% w/v", corresponds to the amount of compound X in grams that is introduced in 100 mL of the composition.

As used herein an "ocular condition" is a disease, ailment or other condition which affects or involves the eye, one of the parts or regions of the eye, or the surrounding tissues such as the lacrimal glands. Broadly speaking, the eye includes the eyeball and the tissues and fluids which constitute the eyeball, the periocular muscles (such as the oblique and rectus muscles), the portion of the optic nerve which is within or adjacent to the eyeball and surrounding tissues such as the lacrimal glands and the eye lids.

As used herein an "anterior ocular condition" is a disease, ailment or condition which affects or which involves an anterior (i.e. front of the eye) ocular region or site, such as a periocular muscle, an eye lid, lacrimal gland or an eye ball tissue or fluid which is located anterior to the posterior wall of the lens capsule or ciliary muscles.

Thus, an anterior ocular condition primarily affects or involves one or more of the following: the conjunctiva, the cornea, the anterior chamber, the iris, the lens, or the lens capsule, and blood vessels and nerves which vascularize or innervate an anterior ocular region or site. An anterior ocular condition is also considered herein as extending to the lacrimal apparatus. In particular, the lacrimal glands which secrete tears, and their excretory ducts which convey tear fluid to the surface of the eye.

Moreover, an anterior ocular condition affects or involves the posterior chamber, which is behind the retina but in front of the posterior wall of the lens capsule.

An anterior ocular condition includes a disease, ailment or condition such as, for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

Anterior ocular conditions also include front of the eye inflammations like inflammation following cataract surgery, glaucoma, anterior chamber inflammation, central macular edema.

A "posterior ocular condition" is a disease, ailment or condition which primarily affects or involves a posterior ocular region or site such as the choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition such as, for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion (CRVO); uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

As used herein the term "microparticle" refers to a particle having a diameter $D_{50}$ of about 1 µm to about 200 µm. The term "nanoparticle" refers to a particle having a diameter $D_{50}$ of less than 1 µm. In exemplary embodiments, the diameter, which can be $D_{50}$, is 1 µm or greater to about 200 µm; and the term "nanoparticle" refers to a particle having a $D_{50}$ of less than about 1 µm.

The term "microsuspension" is intended to mean a composition comprising solid complex microparticles suspended in a liquid phase.

As used herein, the expression "to prevent oxidation of the drug" is intended to mean to prevent or delay the oxidation of the drug.

Method for Stabilizing the pH of an Aqueous Composition Comprising a Drug

The present disclosure relates first to a method for stabilizing the pH of an aqueous composition comprising a drug, said method comprising the addition of an additive to prevent oxidation of the drug. The disclosure also relates to an aqueous composition comprising a drug and an additive to prevent oxidation of the drug obtained by this method.

The additive to prevent oxidation of the drug can be added to the aqueous composition before or after the drug.

Drug

The aqueous composition of the disclosure comprises a drug. In the context of the disclosure, the drug is an ophthalmic drug, i.e. a compound that exhibits a therapeutic effect when administered in a sufficient amount to a patient suffering from an ocular condition.

In an embodiment, the drug is a corticosteroid, which includes glucocorticoids and mineralocorticoids. Advantageously, the drug is selected from betamethasone-type corticosteroids which are glucocorticoids having a $C_{16}$ methyl substitution. Betamethasone-type corticosteroids include alclometasone, bed ometasone, betamethasone, clobetasone, clocortolone, deoxymethasone, dexamethasone, diflucortolone, flumethasone, fluocortolone, fluprednidene, fluticasone, halometasone, and mometasone. Preferably, the drug is dexamethasone.

In a specific embodiment, the drug is prone to oxidation, which means that the drug can be degraded via an oxidation pathway. In some cases, the degradation products of this oxidation are acidic degradation products, and the addition of an additive to prevent oxidation of the drug prevents the formation of the acidic degradation products.

The concentration of the drug in the aqueous composition of the disclosure may be from about 0.1 mg/ml to about 100 mg/ml, in particular from about 1 mg/ml to about 100 mg/ml, in particular from about 1 mg/ml to about 50 mg/ml, more particularly from about 1 mg/ml to about 40 mg/ml, even more particularly from about 5 mg/ml to about 35 mg/ml, more particularly still from about 10 mg/ml to about 30 mg/ml. The concentration of the drug in the aqueous composition of the disclosure may be from about 5 mg/ml to about 30 mg/ml, in particular from about 10 mg/ml to about 25 mg/ml.

The amount of drug in the aqueous composition may be from 0.5 to 5%, in particular from 1 to 4%, and more particularly from 1.5 to 3%, by weight of drug based on the volume of the composition.

Cyclodextrin

The aqueous composition can comprise cyclodextrin. The amount of cyclodextrin in the aqueous composition may be from 1 to 35%, in particular 5 to 30%, more particularly 10 to 27%, even more particularly 12 to 25%, by weight of cyclodextrin based on the volume of the composition. The amount of cyclodextrin in the aqueous composition may be from 10 to 25%, in particular from 12 to 20%, by weight of cyclodextrin based on the volume of the composition.

Cyclodextrins are cyclic oligosaccharides containing 6 (α-cyclodextrin), 7 (β-cyclodextrin), and 8 (γ-cyclodextrin) glucopyranose monomers linked via α-1,4-glycoside bonds.

α-Cyclodextrin, β-cyclodextrin and γ-cyclodextrin are natural products formed by microbial degradation of starch. The outer surface of the doughnut shaped cyclodextrin molecules is hydrophilic, bearing numerous hydroxyl groups, but their central cavity is somewhat lipophilic (Kurkov, S. V., Loftsson, T., 2013. Cyclodextrins. Int J Pharm 453, 167-180; Loftsson, T., Brewster, M. E., 1996. Pharmaceutical applications of cyclodextrins. 1. Drug solubilization and stabilization. Journal of Pharmaceutical Sciences 85, 1017-1025). In addition to the three natural cyclodextrins, numerous water-soluble cyclodextrin derivatives have been synthesized and tested as drug carriers, including cyclodextrin polymers (Stella, V. J., He, Q., 2008. Cyclodextrins. Tox. Pathol. 36, 30-42).

Cyclodextrins can enhance the solubility and bioavailability of hydrophobic compounds. In aqueous solutions, cyclodextrins form inclusion complexes with many drugs by taking up a drug molecule, or more frequently some lipophilic moiety of the molecule, into the central cavity. This property has been used for drug formulation and drug delivery purposes. Formation of drug/cyclodextrin inclusion complexes, their effect on the physicochemical properties of drugs, their effect on the ability of drugs to permeate biomembranes and the usage of cyclodextrins in pharmaceutical products have been reviewed (Loftsson, T., Brewster, M. E., 2010. Pharmaceutical applications of cyclodextrins: basic science and product development. Journal of Pharmacy and Pharmacology 62, 1607-1621; Loftsson, T., Brewster, M. E., 2011. Pharmaceutical applications of cyclodextrins: effects on drug permeation through biological membranes. J. Pharm. Pharmacol. 63, 1119-1135; Loftsson, T., Jarvinen, T., 1999. Cyclodextrins in ophthalmic drug delivery. Advanced Drug Delivery Reviews 36, 59-79).

Cyclodextrins and drug/cyclodextrin complexes are able to self-assemble in aqueous solutions to form nano- and micro-sized aggregates and micellar-like structures that are also able to solubilize poorly soluble drugs through non-inclusion complexation and micellar-like solubilization (Messner, M., Kurkov, S. V., Jansook, P., Loftsson, T., 2010. Self-assembled cyclodextrin aggregates and nanoparticles. Int J Pharm 387, 199-208). In general, the tendency of cyclodextrins to self-assemble and form aggregates increases upon formation of drug/cyclodextrin complexes and the aggregation increases with increasing concentration of drug/cyclodextrin complexes. In general, hydrophilic cyclodextrin derivatives, such as 2-hydroxypropyl-β-cyclodextrin and 2-hydroxypropyl-γ-cyclodextrin, and their complexes are freely soluble in water. On the other hand, the natural α-cyclodextrin, β-cyclodextrin and γ-cyclodextrin and their complexes have limited solubility in pure water or 129.5±0.7, 18.4±0.2 and 249.2±0.2 mg/ml, respectively, at 25° C. (Sabadini E., Cosgrovea T. and do Carme Egidio F., 2006. Solubility of cyclomaltooligosaccharides (cyclodextrins) in $H_2O$ and $D_2O$: a comparative study. Carbohydr Res 341, 270-274). It is known that their solubility increases somewhat with increasing temperature (Jozwiakowski, M. J., Connors, K. A, 1985. Aqueous solubility behavior of three cyclodextrins. Carbohydr. Res., 143, 51-59). Due to the limited solubility of their complexes, the natural cyclodextrins most often display Bs-type or Bi-type phase-solubility diagrams (Brewster M. E., Loftsson T., 2007, Cyclodextrins as pharmaceutical solubilizers. Adv. Drug Deliv. Rev., 59, 645-666). It has been observed that solubility of the natural cyclodextrins can decrease below their solubility in pure water upon formation of drug/cyclodextrin complexes (Jansook, P., Maya-Ortega, M. D., Loftsson, T., 2010. Effect of self-aggregation of γ-cyclodextrin on drug solubilization. Journal of Inclusion Phenomena and Macrocyclic Chemistry 68, 229-236). The low concentration of dissolved drug/cyclodextrin complexes hampers formation of nano- and microparticles containing drug/cyclodextrin complexes. Furthermore, other excipients, such as water-soluble polymers used to stabilize nano- and microsuspensions, can form complexes with cyclodextrins and, thus, hamper formation of drug/cyclodextrin complexes even further.

Previously, Applicants have described preparation and testing of cyclodextrin-based eye drops containing dexamethasone (Johannesson, G., Moya-Ortega, M. D., Asgrimsdottir, G. M., Lund, S. H., Thorsteinsdottir, M., Loftsson, T., Stefansson, E., 2014. Kinetics of γ-cyclodextrin nanoparticle suspension eye drops in tear fluid. Acta Ophthalmologica 92, 550-556; Thorsteinn Loftsson and Einar Stefansson, Cyclodextrin nanotechnology for ophthalmic drug delivery, U.S. Pat. No. 7,893,040 (Feb. 22, 2011); Thorsteinn Loftsson and Einar Stefansson, Cyclodextrin nanotechnology for ophthalmic drug delivery, U.S. Pat. No. 8,633,172 (Jan. 21, 2014); Thorsteinn Loftsson and Einar Stefansson, Cyclodextrin nanotechnology for ophthalmic drug delivery U.S. Pat. No. 8,999,953 (Apr. 7, 2015)), dorzolamide (Johannesson, G., Maya-Ortega, M. D., Asgrimsdottir, G. M., Lund, S. H., Thorsteinsdottir, M., Loftsson, T., Stefansson, E., 2014. Kinetics of γ-cyclodextrin nanoparticle suspension eye drops in tear fluid. Acta Ophthalmologica 92, 550-556; Gudmundsdottir, B. S., Petursdottir, D., Asgrimsdottir, G. M., Gottfredsdottir, M. S., Hardarson, S. H., Johannesson, G., Kurkov, S. V., Jansook, P., Loftsson, T., Stefansson, E., 2014. γ-Cyclodextrin nanoparticle eye drops with dorzolamide: effect on intraocular pressure in man. J. Ocul. Pharmacol. Ther. 30, 35-41), irbesartan (Muankaew, C., Jansook, P., Stefansson, E., Loftsson, T., 2014. Effect of γ-cyclodextrin on solubilization and complexation of irbesartan: influence of pH and excipients. Int J Pharm 474, 80-90), telmisartan (C. Muankaew, P. Jansook, H. H. Sigurosson, T. Loftsson, 2016, Cyclodextrin-based telmisartan ophthalmic suspension: Formulation development for water-insoluble drugs. Int. J. Pharm. 507, 21-31) and cyclosporin A (S. Johannsdottir, P. Jansook, E. Stefansson, T. Loftsson, 2015, Development of a cyclodextrin-based aqueous cyclosporin A eye drop formulation. Int. J. Pharm. 493(1-2), 86-95) in cyclodextrin nanoparticles. The studies show that the nanoparticles increase the drug contact time with the ocular surface and the ocular bioavailability of the drugs. The drug/cyclodextrin nano- and microparticles are not only retained on the eye surface but also enhance drug solubility in the aqueous tear fluid. Nano- and microparticles composed of drug/γ-cyclodextrin complexes have been shown to be especially effective drug carriers for topical delivery of drug into the eye.

The composition of the disclosure can comprise a solid complex comprising a drug and a cyclodextrin. The complex comprising a drug and a cyclodextrin may be referred to as a "drug/cyclodextrin complex". When the drug is a corticosteroid, the complex comprising a corticosteroid and cyclodextrin may be referred to as a "corticosteroid/cyclodextrin complex". When the drug is dexamethasone and the cyclodextrin is γ-cyclodextrin, the complex comprising dexamethasone and γ-cyclodextrin may be referred to as a "dexamethasone/γ-cyclodextrin complex".

The solid complex of the composition of the disclosure may be a complex aggregate. The complex aggregate may correspond to an aggregate of a plurality of complexes, in particular a plurality of inclusion complexes comprising a drug and a cyclodextrin, typically complexes comprising a drug and γ-cyclodextrin.

According to one embodiment, the aqueous composition of the disclosure is a microsuspension.

In particular, the aqueous composition of the disclosure comprises a solid complex that has a diameter $D_{50}$ of less than about 100 µm, in particular about 1 µm to about 100 µm. In one embodiment, the diameter $D_{50}$ may be in the range of about 1 µm to about 25 µm, in particular about 1 µm to about 20 µm, more particularly about 1 µm to about 10 µm, even more particularly about 2 µm to about 10 µm, more particularly still about 2 µm to about 5 µm or about 3 µm to about 8 µm. The diameter and/or size of a particle or complex can be measured according to any method known to those of ordinary skill in the art. For example, the diameter $D_{50}$ is measured by laser diffraction particle size analysis. Generally, there are a limited number of techniques for measuring/evaluating cyclodextrin/drug particle or complex diameter and/or size. In particular, persons of ordinary skill in this field know that the physical properties (e.g. particle size, diameter, average diameter, mean particle size, etc.) are typically evaluated/measured using such limited, typical known techniques. For example, such known techniques are described in Int. J. Pharm. 493 (2015), 86-95, which is incorporated by reference herein in its entirety. In addition, such limited, known measurement/evaluation techniques were known in the art as evidenced by other technical references such as, for example, European Pharmacopoeia (2.9.31 Particle size analysis by laser diffraction, January 2010), and Saurabh Bhatia, Nanoparticles types, classification, characterization, fabrication methods and drug delivery applications, Chapter 2, Natural Polymer Drug Delivery Systems, PP. 33-94, Springer, 2016, which are also incorporated by reference herein in their entireties.

European Pharmacopoeia (01/2008:1163) teaches that eye drops in the form of a suspension should comply with the following: for each 10 µg of solid active substance, not more than about 20 particles have a maximum dimension greater than about 25 µm, and not more than about 2 of these particles have a maximum dimension greater than about 50 µm. None of the particles can have a maximum dimension greater than about 90 µm. The aqueous compositions of the disclosure are in conformity with the requirements of European Pharmacopoeia (01/2008:1163).

In general, it is recommended that particle sizes in aqueous eye drop suspensions are kept to a minimum, preferable below about 10 µm, to prevent eye irritation. Furthermore, the sedimentation rate in aqueous suspensions is proportional to the particle diameter, the sedimentation rate of large particles is faster than that of small particles assuming all other factors remaining constant.

In particular, 60 to 95% by weight, more particularly 70 to 90% by weight, of the drug in the composition may be in the form of a solid complex of drug and cyclodextrin.

Even more particularly, 5 to 40% by weight, in particular 10 to 30% by weight, of the drug in the composition may be in dissolved form. The dissolved form includes uncomplexed drug that is dissolved in the liquid phase and complexes of drug and cyclodextrin that are dissolved in the liquid phase as well as water-soluble nanoparticles consisting of drug/cyclodextrin complex aggregates.

Preferably, 0% to 0.5% by weight of the drug in the composition may be in uncomplexed solid form. As such, the composition of the disclosure may be substantially free of solid uncomplexed particles of drug.

In one embodiment, the microsuspension may comprise about 70% to about 99% of the drug in microparticles and about 1% to about 30% of the drug in nanoparticles. More particularly, the microsuspension may comprise about 80% to about 95% of the drug in microparticles having a diameter of about 1 µm to about 10 µm, and about 20% to about 5% of the drug in nanoparticles. The microsuspension may comprise about 80% of the drug in microparticles having a diameter of about 1 µm to about 10 µm, and about 20% of the drug in nanoparticles.

In another embodiment, the microsuspension may comprise about 40% to about 99% of the drug in microparticles and about 1% to about 60% of the drug in nanoparticles or water-soluble drug/cyclodextrin complexes. In particular, the microsuspension may comprise about 80% to about 95% of the drug in microparticles having a diameter of about 1 µm to about 10 µm, and about 5% to about 20% of the drug in nanoparticles or water-soluble active pharmaceutical ingredient/cyclodextrin complexes.

According to a preferred embodiment, the aqueous composition comprises drug/cyclodextrin complexes, preferably corticosteroid/cyclodextrin complexes, and more preferably dexamethasone/γ-cyclodextrin complexes.

Examples of compositions comprising drug/cyclodextrin complexes are disclosed in WO2018/100434, which is hereby incorporated by reference.

Additive to Prevent Oxidation of the Drug

The aqueous composition comprises an additive to prevent the oxidation of the drug. Applicants surprisingly found that the addition of an additive to prevent the oxidation of the drug stabilizes the pH of the aqueous composition, and prevents the drop of pH.

In a preferred embodiment, the additive to prevent the oxidation of the drug is selected from antioxidants, oxygen scavengers and mixtures thereof.

Antioxidants typically include phenolic antioxidant and reducing agent. Phenolic antioxidants are sterically hindered phenols that react with free radicals, blocking the oxidation reaction. Among phenolic antioxidants, one can cite butylated hydroxyanisole (BHA), butylated hydroxytoluene (BHT), tert-butylhydroquinone (TBHQ) or 3,4-dhydroxybenzoic acid, dodecyl 3,4,5-trihydroxybenzoate (lauryl gallate). Reducing agent are compounds that have lower redox potential than the drug they are intended to prevent from oxidation. Reducing agents scavenger oxygen from the medium and thus delay or prevent oxidation. Among reducing agents, one can cite sodium thiosulfate (STS) or other industrial food preservatives with antioxidant properties. Examples of antioxidants further include water soluble natural antioxidants such as ascorbic acid, malic acid, citric acid, tartaric acid, lactic acid, and other organic acids and their derivatives. Other antioxidants may further be selected among known food antioxidants.

In a specific embodiment, the additive to prevent the oxidation of the drug is sodium thiosulfate.

In another specific embodiment, the additive to prevent the oxidation of the drug is selected among sodium thiosulfate, methionine, 3,4-dihydroxybenzoic acid, sodium citrate, malic acid, sodium ascorbate, tartaric acid, α-monothioglycerol, butylated hyroxyanisole, lauryl gallate, lactic acid, tert-butylhydroquinone, and their salts or derivatives, or mixtures thereof. More preferably, said additive is selected among sodium thiosulfate, methionine (typically L-methionine), 3,4-dihydroxybenzoic acid, sodium citrate (e.g. sodium citrate tribasic dehydrate), malic acid (typically DL-malic acid, sodium ascorbate (e.g. (+)-sodium L-ascorbate), tartaric acid (typically DL-tartaric acid), α-monothioglycerol, and butylated hyroxyanisole, and even more preferably, said additive is selected among sodium thiosulfate, methionine, and, 3,4-dihydroxybenzoic acid, Of course, a mixture of said antioxidants may be added as additive to prevent the oxidation of the drug.

The additive to prevent the oxidation of the drug, typically sodium thiosulfate, methionine, or 3,4 dihydroxybenzoic acid, can be added at a concentration of at least 0.05% (w/v), preferably at a concentration between 0.05% (w/v) and 1% (w/v), more preferably between 0.1 to 0.5%, and still more preferably between 0.2% (w/v) and 0.4% (w/v). The additive to prevent the oxidation of the drug, typically sodium thiosulfate, can be added at a concentration between 0.2% (w/v) and 0.3% (w/v).

As used herein, the concentration of 0.3% (w/v) sodium thiosulfate corresponds to water-free sodium thiosulfate. This corresponds to 0.471 g/100 mL of sodium thiosulfate pentahydrate. For other antioxydants, typically the molar equivalent of 0.3% sodium thiosulfate may be used in the aqueous composition.

pH of the Composition

Advantageously, the pH of the aqueous composition comprising a drug is between 4 and 9, preferably between 5 and 8. Typically, the pH of the aqueous composition comprising a drug is physiological pH.

Advantageously, the pH of the aqueous composition comprising a corticosteroid is between 4 and 8, preferably between 4.5 and 6.

In a specific embodiment, the pH of the aqueous composition is stabilized between 4 and 8, preferably between 4.5 and 6, for more than 6 months, preferably more than 9 months, when stored at 25° C., 40% relative humidity, according to ICH guidelines.

Aqueous Composition

Advantageously, the aqueous composition is an ophthalmically acceptable medium. The term "ophthalmically acceptable medium" is intended to mean a medium suitable for ophthalmic administration of the composition. The ophthalmically acceptable medium is preferably a liquid.

The aqueous composition can comprise organic solvent. In the present case, the aqueous composition preferably does not comprise organic solvent.

In a particular embodiment, the ophthalmically acceptable medium does not comprise any other solvent than water. The ophthalmically acceptable medium may thus correspond to an aqueous eye drop vehicle. In a specific embodiment, the aqueous composition is an unbuffered aqueous eye drop vehicle.

According to a specific embodiment the aqueous composition comprises water and optionally an additive selected from the group consisting of a preservative, a stabilizing agent, an electrolyte, and combinations thereof. In particular, the ophthalmically acceptable medium may comprise a preservative.

A preservative may be used to limit bacterial proliferation in the composition. Examples of preservative are benzalkonium chloride, chlorobutanol, thimerosal, phenylmercuric acetate, phenylmercuric nitrate, methylparaben, phenylethyl alcohol, and combinations thereof. The amount of preservative in the composition of the disclosure may be 0 to 1%, in particular 0.001 to 0.5%, more particularly 0.005 to 0.1%, even more particularly 0.01 to 0.04%, by weight of preservative based on the volume of the composition. In a preferred embodiment, the aqueous composition is preservative free.

In particular, the aqueous composition may comprise a stabilizing agent. An example of a suitable stabilizing agent is disodium edetate. The amount of stabilizing agent in the composition of the disclosure may be 0 to 1%, in particular 0.01 to 0.5%, more particularly 0.08 to 0.2% by weight of stabilizing agent based on the volume of the composition.

In particular, the ophthalmically acceptable medium may comprise an electrolyte. An electrolyte may especially be used to make the composition isotonic. Examples of suitable electrolytes include sodium chloride, potassium chloride, and combinations thereof. Preferably, the electrolyte is sodium chloride. The amount of electrolyte in the composition of the disclosure may be 0 to 2%, in particular 0.1 to 1.5%, more particularly 0.2 to 1% by weight of electrolyte based on the volume of the composition.

The aqueous composition may further comprise a polymer. In particular, said polymer may be a water-soluble polymer. Moreover, said polymer may be a viscosity enhancing polymer. The term "viscosity enhancing polymer" is intended to mean a polymer that increases the viscosity of a liquid. The polymer increases the viscosity of the composition of the disclosure. The increase of viscosity results is an enhanced physical stability of the composition. As such, the composition is less prone to sedimentation of the solid complex when it comprises a polymer. The polymer may thus be considered as a polymeric stabilizing agent. In particular, the polymer may be a surface active polymer. The term "surface active polymer" is intended to mean a polymer that exhibits surfactant properties. Surface active polymers may, for example, comprise hydrophobic chains grafted to a hydrophilic backbone polymer; hydrophilic chains grafted to a hydrophobic backbone; or alternating hydrophilic and hydrophobic segments. The first two types are called graft copolymers and the third type is named block copolymer.

In one embodiment, the ophthalmic composition of the disclosure comprises a polymer selected from the group consisting of a polyoxyethylene fatty acid ester; a polyoxyethylene alkylphenyl ether; a polyoxyethylene alkyl ether; a cellulose derivative such as alkyl cellulose, hydroxyalkyl cellulose and hydroxyalkyl alkylcellulose; a carboxyvinyl polymer such as a carbomer, for example Carbopol 971 and Carbopol 974; a polyvinyl polymer; a polyvinyl alcohol; a polyvinylpyrrolidone; a copolymer of polyoxypropylene and polyoxyethylene; tyloxapol; and combinations thereof.

Examples of suitable polymers include, but are not limited to, polyethylene glycol monostearate, polyethylene glycol distearate, hydroxypropyl methylcellulose, hydroxypropylcellulose, polyvinylpyrrolidone, polyoxyethylene lauryl ether, polyoxyethylene octyldodecyl ether, polyoxyethylene stearyl ether, polyoxyethylene myristyl ether, polyoxyethylene oleyl ether, sorbitan esters, polyoxyethylene hexadecyl ether (e.g., cetomacrogol 1000), polyoxyethylene castor oil derivatives, polyoxyethylene sorbitan fatty acid esters (e.g., Tween 20 and Tween 80 (ICI Specialty Chemicals)); polyethylene glycols (e.g., Carbowax 3550 and 934 (Union Carbide)), polyoxyethylene stearates, carboxymethylcellulose calcium, carboxymethylcellulose sodium, methylcellulose, hydroxyethylcellulose, hydroxypropyl methylcellulose, cellulose, polyvinyl alcohol (PVA), poloxamers (e.g., Pluronics F68 and F108, which are block copolymers of ethylene oxide and propylene oxide); poloxamines (e.g., Tetronic 908, also known as Poloxamine 908, which is a tetrafunctional block copolymer derived from sequential addition of propylene oxide and ethylene oxide to ethylenediamine (BASF Wyandotte Corporation, Parsippany, N.J.)); Tetronic 1508 (T-1508) (BASF Wyandotte Corporation), Tritons X-200, which is an alkyl aryl polyether sulfonate (Rohm and Haas); PEG-derivatized phospholipid, PEG-derivatized cholesterol, PEG-derivatized cholesterol derivative, PEG-derivatized vitamin A, PEG-derivatized vitamin E, random copolymers of vinyl pyrrolidone and vinyl acetate, combinations thereof and the like.

Particularly preferred examples of polymers according to the disclosure are tyloxapol and a copolymer of polyoxypropylene and polyoxyethylene.

More particularly, the copolymer of polyoxypropylene and polyoxyethylene may be a triblock copolymer comprising a hydrophilic block-hydrophobic block-hydrophilic block configuration.

In one embodiment, the composition of the disclosure comprises a polymer which is a poloxamer. Poloxamers can include any type of poloxamer known in the art. Poloxamers include poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, poloxamer 105 benzoate and poloxamer 182 dibenzoate. Poloxamers are also referred to by their trade name Pluronic such as Pluronic 10R5, Pluronic 17R2, Pluronic 17R4, Pluronic 25R2, Pluronic 25R4, Pluronic 31 R1, Pluronic F 108, Pluronic F 108, Pluronic F 108, Pluronic F 108NF, Pluronic F 127, Pluronic F 127 NF, Pluronic F 127, Pluronic F 127, Pluronic F 38, Pluronic F 38, Pluronic F 68, Pluronic F 77, Pluronic F 87, Pluronic F 88, Pluronic F 98, Pluronic L 10, Pluronic L 101, Pluronic L 121, Pluronic L 31, Pluronic L 3S, Pluronic L 43, Pluronic L 44, Pluronic L 61, Pluronic L 62, Pluronic L 62 LF, Pluronic L 620, Pluronic L 64, Pluronic L 81, Pluronic L 92, Pluronic L 44, Pluronic N 3, Pluronic P 103, Pluronic P 104, Pluronic P 85, Pluronic P 123, Pluronic P 65, Pluronic P 84, Pluronic P 85, combinations thereof and the like.

Especially useful polymers as stabilizers are poloxamers. Poloxamers can include any type of poloxamer known in the art. Poloxamers include poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 23S, poloxamer 237, poloxamer 238, poloxamer 282, poloxamer 284, poloxamer 288, poloxamer 331, poloxamer 333, poloxamer 334, poloxamer 33S, poloxamer 338, poloxamer 401, poloxamer 402, poloxamer 403, poloxamer 407, poloxamer 105 benzoate and poloxamer 182 di benzoate. Poloxamers are also referred to by their trade name Pluronic such as Pluronic 10R5, Pluronic 17R2, Pluronic 17R4, Pluronic 25R2, Pluronic 25R4, Pluronic 31 R1, Pluronic F 108 Cast Solid Surfacta, Pluronic F 108 NF, Pluronic F 108 Pastille, Pluronic F 108NF Prill Poloxamer 338, Pluronic F 127, Pluronic F 127 NF, Pluronic F 127 NF 500 BHT Prill, Pluronic F 127 NF Prill Poloxamer 407, Pluronic F 38, Pluronic F 38 Pastille, Pluronic F 68, Pluronic F 68 Pastille, Pluronic F 68 LF Pastille, Pluronic F 68 NF, Pluronic F 68 NF Prill Poloxamer 188, Pluronic F 77, Pluronic F 77 Micropastille, Pluronic F 87, Pluronic F 87 NF, Pluronic F 87 NF Prill Poloxamer 237, Pluronic F 88, Pluronic F 88 Pastille, Pluronic F 98, Pluronic L 10, Pluronic L 101, Pluronic L 121, Pluronic L 31, Pluronic L 35, Pluronic L 43, Pluronic L 44 NF Poloxamer 124, Pluronic L 61, Pluronic L 62, Pluronic L 62 LF, Pluronic L 620, Pluronic L 64, Pluronic L 81, Pluronic L 92, Pluronic L44 NF INH surfactant Poloxamer 124 View, Pluronic N 3, Pluronic P 103, Pluronic P 104, Pluronic P 105, Pluronic P 123 Surfactant, Pluronic P 65, Pluronic P 84, Pluronic P 85, combinations thereof and the like. In particular, said polymer is poloxamer 407.

A further polymeric stabilizing agent compatible with the compositions and methods described herein is tyloxapol. In preferred embodiments, the stabilizer and co-solubilizer is tyloxapol, which is a 4-(1,1,3,3-tetramethylbutyl)phenol polymer with formaldehyde and oxirane.

The present disclosure also relates to a method for stabilizing the pH of an aqueous composition comprising corticosteroid/cyclodextrin complexes, said method comprising the addition of an antioxidant to prevent oxidation of the corticosteroid, for example one or more of the antioxidant as described in the previous sections, typically sodium thiosulfate.

The present disclosure also relates to a method for stabilizing the pH of an aqueous composition comprising a drug, said method comprising the use of an oxygen absorber to prevent oxidation of the drug. The aqueous composition comprising a drug can be stored in vials, and the vials can be packaged in sealed pouches, typically aluminium pouches, containing an oxygen absorber. Advantageously, the oxygen absorber contains iron particles.

Aqueous Composition Comprising a Corticosteroid

The present disclosure also relates to an aqueous composition comprising a corticosteroid, cyclodextrin and an additive to prevent oxidation of the corticosteroid, wherein said additive, for example reducing agents, water-soluble natural antioxidants or phenolic antioxidants as described in previous sections, typically sodium thiosulfate, is present in the composition at a concentration between 0.15% (w/v) and 0.45% (w/v), and preferably at a concentration between 0.2% (w/v) and 0.4% (w/v). The additive to prevent the oxidation of the corticosteroid, for example reducing agents, water-soluble natural antioxidants or phenolic antioxidants as described in previous sections, typically sodium thiosulfate, can be present at a concentration between 0.2% (w/v) and 0.3% (w/v).

Corticosteroid

Corticosteroids include glucocorticoids and mineralocorticoids. Advantageously, the corticosteroid is selected from betamethasone-type corticosteroids which are glucocorticoids having a $C_{16}$ methyl substitution. Betamethasone-type corticosteroids include alclometasone, beclometasone, betamethasone, clobetasone, clocortolone, deoxymethasone, dexamethasone, diflucortolone, flumethasone, fluocortolone, fluprednidene, fluticasone, halometasone, and mometasone. Preferably, the drug is dexamethasone.

In a specific embodiment, the corticosteroid is prone to oxidation, which means that the corticosteroid can be degraded via an oxidation pathway. In some cases, the degradation products of this oxidation are acidic degradation products, and the addition of an additive to prevent oxidation of the drug prevents the formation of the acidic degradation products.

The concentration of the corticosteroid in the aqueous composition of the disclosure may be from about 0.1 mg/ml to about 100 mg/ml, in particular from about 1 mg/ml to about 100 mg/ml, in particular from about 1 mg/ml to about 50 mg/ml, more particularly from about 1 mg/ml to about 40 mg/ml, even more particularly about 5 mg/ml to about 35 mg/ml, more particularly still from about 10 mg/ml to about 30 mg/ml. The concentration of the corticosteroid in the aqueous composition of the disclosure may be from about 5 mg/ml to about 30 mg/ml, in particular from about 10 mg/ml to about 25 mg/ml.

The amount of corticosteroid in the aqueous composition may be from 0.5 to 5%, in particular from 1 to 4%, and more particularly from 1.5 to 3%, by weight of corticosteroid based on the volume of the composition.

Cyclodextrin

The aqueous composition comprises cyclodextrin. The amount of cyclodextrin in the aqueous composition may be from 1 to 35%, in particular 5 to 30%, more particularly 10 to 27%, even more particularly 12 to 25%, by weight of cyclodextrin based on the volume of the composition. The amount of cyclodextrin in the aqueous composition may be from 10 to 25%, in particular from 12 to 20%, by weight of cyclodextrin based on the volume of the composition. In certain embodiments with dexamethasone as the drug, the amount of cyclodextrin, typically gamma-cyclodextrin, in the aqueous composition is from 10 to 25% and the amount of dexamethasone is 1.5%. In other embodiments, the amount of cyclodextrin, typically gamma-cyclodextrin in the aqueous composition may be from 20 to 25%, for example 23%, in particular in combination with an amount between 2.0 and 3.5% of dexamethasone, preferably with about 3% of dexamethasone.

The corticosteroid can form a corticosteroid/cyclodextrin complex as described above.

Additive to Prevent Oxidation of the Corticosteroid

The aqueous composition comprises an additive to prevent the oxidation of the corticosteroid. Applicants surprisingly found that the addition of an additive to prevent the oxidation stabilizes the pH of the aqueous composition, and prevents the drop of pH.

In a preferred embodiment, the additive to prevent the oxidation of the corticosteroid is selected from antioxidants, oxygen scavengers and mixtures thereof.

Antioxidants include phenolic antioxidant and reducing agent, such as water-soluble natural antioxidants or other known food antioxidants.

Among phenolic antioxidants, one can cite butylated hydroxyanisole (BHA), butylated hydroxytoluene (BHT), tert-butylhydroquinone (TBHQ) or 3,4-dhydroxybenzoic acid, dodecyl 3,4,5-trihydroxybenzoate (lauryl gallate). Reducing agent are compounds that have lower redox potential than the drug they are intended to prevent from oxidation. Reducing agents scavenger oxygen from the medium and thus delay or prevent oxidation. Among reducing agents, one can cite sodium thiosulfate (STS). Examples of antioxidants further include water soluble natural antioxidants such as ascorbic acid, malic acid, citric acid, tartaric acid, lactic acid, and other organic acids and their derivatives.

Other antioxidants may be selected among known food or cosmetic antioxidants.

In a specific embodiment, the additive to prevent the oxidation of the drug is sodium thiosulfate.

In another specific embodiment, the additive to prevent the oxidation of the drug is selected among sodium thiosulfate, methionine, 3,4-dihydroxybenzoic acid, sodium citrate, malic acid, sodium ascorbate, tartaric acid, α-monothioglycerol, butylated hyroxyanisole, lauryl gallate, lactic acid, tert-butylhydroquinone, and their salts or derivatives. More preferably, said additive is selected among sodium thiosulfate, methionine (typically L-methionine), 3,4-dihydroxybenzoic acid, sodium citrate (e.g. sodium citrate tribasic dehydrate), malic acid (typically DL-malic acid, sodium ascorbate (e.g. (+)-sodium L-ascorbate), tartaric acid (typically DL-tartaric acid), α-monothioglycerol, and butylated hyroxyanisole, and even more preferably, said additive is selected among sodium thiosulfate, methionine, and, 3,4-dihydroxybenzoic acid, Of course, a mixture of said antioxidants may be added as additive to prevent the oxidation of the drug.

pH of the Composition

Advantageously, the pH of the aqueous composition comprising a corticosteroid is between 4 and 8, preferably between 4.5 and 6.

In a specific embodiment, the pH of the aqueous composition is stabilized between 4 and 8, preferably between 4.5 and 6, for more than 6 months, preferably more than 9 months, when stored at 25° C., 40% relative humidity, according to ICH guidelines.

Aqueous Composition

Advantageously, the aqueous composition is an ophthalmically acceptable medium, as described above.

In a particularly preferred embodiment, the aqueous composition comprises:
- 1 to 4% of dexamethasone, for example 1.5% to 3% of dexamethasone;
- 1 to 35% of γ-cyclodextrin, for example 5 to 25% of γ-cyclodextrin;
- 2.2 to 2.8% of polymer, or 2.8 to 3.2%, for example 2.5% or 3.0% of polymer, typically poloxamer;
- 0 to 0.2% of stabilizing agent, for example 0.1% of stabilizing agent, typically, disodium edetate;
- 0.15 to 0.45% of an additive to prevent the oxidation of the corticosteroid, for example between 0.2% and 0.4%, or between 0.2% and 0.3%, of an additive to prevent the oxidation of the corticosteroid, typically phenolic antioxidants or reducing agents, such as water-soluble natural antioxidants, and more preferably sodium thiosulfate, L-methionine, or 3,4-dihydroxybenzoic acid;
- 0 to 1% of electrolyte, for example 0.57% of electrolyte, typically sodium chloride; and
- water;

wherein the % are % by weight based on the volume of the composition.

The aqueous composition comprising a corticosteroid, cyclodextrin and an additive to prevent oxidation of the corticosteroid can be stored in plastic vials, typically LDPE vials, or glass vials.

Preferred Aqueous Composition with Dexamethasone

In a particular embodiment, an aqueous composition comprises or essentially consists of;
- 1 to 4% of dexamethasone, for example 1.5% to 3% of dexamethasone;
- 1 to 35% of γ-cyclodextrin, for example 5 to 25% of γ-cyclodextrin;
- 0 to 0.2% of stabilizing agent, for example 0.1% of stabilizing agent, typically, disodium edetate;
- 0 to 1% of electrolyte, for example 0.57% of electrolyte, typically sodium chloride; and
- water;

wherein the % are % by weight based on the volume of the composition.

In a particular embodiment, an aqueous composition for use as described in the present specification comprises or essentially consists of;
- 1 to 4% of dexamethasone, for example 1.5% to 3% of dexamethasone;
- 1 to 35% of γ-cyclodextrin, for example 5 to 25% of γ-cyclodextrin;
- optionally 2.2 to 2.8% of polymer or 2.8% to 3.2% of polymer, for example 2.5% or 3.0% of polymer, typically poloxamer;

0 to 0.2% of stabilizing agent, for example 0.1% of stabilizing agent, typically, disodium edetate;

0% to 0.8% of an additive to prevent the oxidation of the dexamethasone, for example between 0.1% and 0.5%, or between 0.2% and 0.4%, of an additive to prevent the oxidation of the corticosteroid, typically phenolic antioxidants or reducing agents, such as water-soluble natural antioxidants, and more preferably sodium thiosulfate, L-methionine, or 3,4-dihydroxybenzoic acid;

0 to 1% of electrolyte, for example 0.57% of electrolyte, typically sodium chloride; and water;

wherein the % are % by weight based on the volume of the composition.

More specifically, a particularly preferred embodiment is an eye drop formulation comprising or essentially consisting of:

1.5% of dexamethasone;
14% of γ-cyclodextrin;
2.5% of poloxamer;
0 to 0.2% of stabilizing agent, for example 0.1% of disodium edetate;
0 to 1% of electrolyte, for example 0.57% of sodium chloride;
0% to 0.6% of an additive to prevent the oxidation of the dexamethasone, for example between 0.2% and 0.4%, of an additive to prevent the oxidation of the corticosteroid, typically phenolic antioxidants or reducing agents, such as water-soluble natural antioxidants, and more preferably sodium thiosulfate, L-methionine, or 3,4-dihydroxybenzoic acid;

and
water;

wherein the % are % by weight based on the volume of the composition.

Typically, an eye drop formulation has the following components:

1.5% of dexamethasone;
14% of γ-cyclodextrin;
2.5% of poloxamer;
0.1% of disodium edetate;
0.57% of sodium chloride; and
between 0.2% and 0.4% of sodium thiosulfate;
water;

Another particular embodiment is an eye drop formulation comprising or essentially consisting of:

3% of dexamethasone;
1 to 35% of γ-cyclodextrin, for example 20 to 25% of γ-cyclodextrin;
optionally 2.8 to 3.2% of polymer, for example 3.0% of polymer, typically poloxamer;
0 to 0.2% of stabilizing agent, for example 0.1% of stabilizing agent, typically, disodium edetate;
0% to 0.6% of an additive to prevent the oxidation of the dexamethasone, for example between 0.1% and 0.5%, or between 0.2% and 0.4%, of an additive to prevent the oxidation of the corticosteroid, typically phenolic antioxidants or reducing agents, such as water-soluble natural antioxidants, and more preferably sodium thiosulfate, L-methionine, or 3,4-dihydroxybenzoic acid;
0 to 1% of electrolyte, for example 0.57% of electrolyte, typically sodium chloride; and
water;

wherein the % are % by weight based on the volume of the composition.

Another particular embodiment is an eye drop formulation comprising or essentially consisting of:

3% of dexamethasone;
between 20 and 25% of γ-cyclodextrin;
optionally between 2.8 and 3.2% of poloxamer; for example 3.0% of poloxamer;
0 to 0.2% of stabilizing agent, for example 0.1% of disodium edetate;
0 to 1% of electrolyte, for example 0.57% of sodium chloride;
0% to 0.6% of an additive to prevent the oxidation of the dexamethasone, for example between 0.1% and 0.5%, or between 0.2% and 0.4%, of an additive to prevent the oxidation of the corticosteroid, typically phenolic antioxidants or reducing agents, such as water-soluble natural antioxidants, and more preferably sodium thiosulfate, L-methionine, or 3,4-dihydroxybenzoic acid;

and
water;

wherein the % are % by weight based on the volume of the composition.

Typically, an eye drop formulation have the following components:

3% of dexamethasone;
between 20 and 25% of γ-cyclodextrin; for example 23% of γ-cyclodextrin;
between 2.8 and 3.2% of poloxamer;
0.1% of disodium edetate;
0.57% of sodium chloride; and
between 0.2% and 0.4% of sodium thiosulfate; typically 0.3% of sodium thiosulfate,
water;

All the above-described formulations or aqueous compositions are advantageously preservative free.

The final formulation for use as an eye drop is a microsuspension including complex aggregates of dexamethasone and γ-cyclodextrin. Typically, 60 to 95% by weight, more particularly, 70 to 90% by weight of the dexamethasone in the composition may be in the form of a solid complexes of dexamethasone and γ-cyclodextrin.

Methods for preparing such formulations comprise the steps of:

a) mixing the dexamethasone in an ophthalmically acceptable medium with the other excipients and heating until the dexamethasone is substantially dissolved in the ophthalmically acceptable medium; for example at least 60 minutes at a temperature between 80° C. and 110° C., b) suspending gamma cyclodextrin in an ophthalmically acceptable medium to form a suspension and heating said suspension until the cyclodextrin is substantially dissolved in the ophthalmically acceptable medium;

c) mixing the compositions of step a) and b) at a temperature T1 lower than 120° C. and heating the mixture at a temperature T1 lower than 120° C. for a time t; and d) cooling the resulting solution to a temperature T2 to obtain an aqueous composition comprising a solid complex of dexamethasone and a cyclodextrin (preferably gamma cyclodextrin).

In the above manufacturing method, the dexamethasone may be suspended in an ophthalmically acceptable medium free of cyclodextrin, optionally with the other excipients. The resulting suspension may have a milky appearance. Separately gamma cyclodextrin may be suspended in an ophthalmically acceptable medium free of active pharmaceutical ingredient. The resulting suspension may have a milky appearance. The two suspensions may be heated or sterilized by, for example, heating in an autoclave for 121° C. for 20 minutes. Then the two suspensions or hot solutions may be mixed together and the mixture may be heated until the complex of dexamethasone and gamma-cyclodextrin is formed. The resulting solution may be cooled at a rate sufficient to produce a microsuspension comprising a solid active pharmaceutical ingredient/gamma-cyclodextrin complex.

Detailed methods for manufacturing the microsuspensions are also described in WO2018100434.

Such microsuspension as above-described are stable and may be used as an eye drop formulation.

In specific embodiments, said aqueous compositions with 1.5% (w/v) are ophthalmic microsuspensions, preservative-free. They may be presented in unit doses of 0.5 ml fill volume, for example in LDPE plastic material. The resulting suspension may be stored at ambient temperature, below 25° C., and stored for at least 2, 3, 6, 12, 18 or 24 months.

Use of the Aqueous Composition Comprising a Corticosteroid

The aqueous compositions of the disclosure may be for use in the treatment of an ocular condition, in particular an anterior ocular condition or a posterior ocular condition, more particularly uveitis, macular edema, macular degeneration, retinal detachment, ocular tumors, fungal or viral infections, multifocal choroiditis, diabetic retinopathy, proliferative vitreoretinopathy (PVR), sympathetic ophthalmia, Vogt Koyanagi-Harada (VKH) syndrome, histoplasmosis, uveal diffusion, and vascular occlusion. The aqueous compositions of the disclosure may be particularly useful in treating uveitis, macular edema, diabetic retinopathy, proliferative vitreoretinopathy (PVR), and vascular occlusions.

The aqueous compositions comprising dexamethasone according to the disclosure may in particular be used for the treatment of macular edema. In this case, the aqueous compositions comprising dexamethasone according to the disclosure may be topically administered to the eye in an amount of 1 drop of composition three times per day. The amount of dexamethasone in said composition may be from 1 to 5%, in particular 1.5% to 3% by weight of dexamethasone based on the volume of the composition.

The compositions of the disclosure comprising dexamethasone do not need to be administered as frequently as known topical dexamethasone compositions, i.e. 1 drop of composition six times per day. Indeed, due to the viscosity of the composition, the solid complexes of the composition of the disclosure exhibit higher contact time on the surface of the eye compared to known compositions which increases the bioavailability of the drug.

The present disclosure also covers the use of the aqueous composition of the disclosure as an eye drop solution.

In an embodiment, the aqueous compositions comprising dexamethasone according to the disclosure may in particular be used for the treatment of central retinal vein occlusion or eye inflammations like inflammation following cataract surgery, glaucoma, anterior chamber inflammation, central macular edema.

The present disclosure also relates to the use of the aqueous composition of the disclosure for the manufacture of a medicament for the treatment of an ocular condition, in particular an anterior ocular condition or a posterior ocular condition. The aqueous compositions of the disclosure may be particularly useful in the manufacture of a medicament for the treatment of central retinal vein occlusion or eye inflammations like inflammation following cataract surgery, glaucoma, anterior chamber inflammation, central macular edema.

The disclosure also relates to a method for treating an ocular condition, in particular an anterior ocular condition or a posterior ocular condition, the method comprising administering to a subject in need thereof, preferably a human, a therapeutically efficient amount of the aqueous composition of the disclosure.

As used herein, the term "treating" includes reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

As used herein, the terms "therapeutically efficient amount" refer to an amount of the drug that will elicit the biological or medical response of a subject, for example, ameliorate the symptoms, alleviate conditions, slow or delay disease progression, or prevent a disease.

Preferred Use of Eye Drop Formulations with Dexamethasone

The aqueous compositions and eye drop formulations with dexamethasone as described above are preferably used in the treatment or prevention of
  diabetic macular edema;
  inflammation following ocular surgery, typically following cataract surgery;
  Cystoid Macular Edema following ocular surgery;
  Acute anterior uveitis;
  Dry Eye Disease and Blepharitis;
  Other acute or chronic ocular inflammatory disorders, such as Graft vs Host Disease (GVHD), vernal conjunctivitis, pterygium, chalazion, or allergic conjunctivitis;
  Post corneal transplantation to control inflammation and prevent rejection; or,
  Treatment of non-infectious uveitis affecting the posterior segment of the eye.

Specific embodiments of such use are described in more detail in the next section.

Methods of Treating Diabetic Macular Edema

The eye drop formulations of the present disclosure have been tested in clinical trials in patients suffering from such disorders and the results are provided in the Examples. In particular, efficacy has been shown for treating diabetic macular edema with eye drop formulation of 1.5% (w/v) dexamethasone.

More specifically, it is provided here a method of treating diabetic macular edema in a subject in need thereof, said method comprising topically administering to an affected eye of said subject, a therapeutically efficient amount of an eye drop formulation comprising 1.5% (w/v) dexamethasone (typically one of the preferred formulations as described above), preferably with a dosing of one, two, three, four, five, or six drops a day, for example for a duration of at least 6, 7, 8, 9, 10, 11, or 12 weeks.

In a preferred embodiment of the method, the eye drop formulation for use in the above method, comprises or essentially consists of:
  1.5% of dexamethasone;
  14% of γ-cyclodextrin;
  2.5% of poloxamer;
  0 to 0.2% of stabilizing agent, for example 0.1% of disodium edetate;

0 to 1% of electrolyte, for example 0.57% of sodium chloride;

0% to 0.6% of an additive to prevent the oxidation of the dexamethasone, for example between 0.1% and 0.5%, or between 0.2% and 0.4%, of an additive to prevent the oxidation of the corticosteroid, typically sodium thiosulfate;

and water;

wherein the % are % by weight based on the volume of the composition.

In a preferred embodiment of the method, the eye drop formulation for use in the above method, comprises or essentially consists of:

3% of dexamethasone;
between 20% and 25% of γ-cyclodextrin; for example, 23% of γ-cyclodextrin;
2.5% of poloxamer;
0 to 0.2% of stabilizing agent, for example 0.1% of disodium edetate;
0 to 1% of electrolyte, for example 0.57% of sodium chloride;
0% to 0.6% of an additive to prevent the oxidation of the dexamethasone, for example between 0.1% and 0.5%, or between 0.2% and 0.4%, of an additive to prevent the oxidation of the corticosteroid, typically sodium thiosulfate;

and water;

wherein the % are % by weight based on the volume of the composition.

Typically, the central macular thickness (CMT), as assessed by SD-OCT may be significantly reduced after 12 weeks of such above treatment in a patient suffering from DME, for example of more than 10% CMT as measured from baseline, CMT being determined as described in the Examples below.

In addition, the pin-hole visual acuity may be improved from baseline to at least 3 ETDRS letters after 12 weeks of the above treatment in patients suffering from DME. Pin-hole visual acuity may be determined as described in the Examples below.

The present treatment is particularly useful for patients with no or inadequate response to VEGF inhibitor treatments (VEGFi naïve patients) and/or which do not support invasive treatments for diabetic macular edema.

Hence, in a particular embodiment of the above method for treating diabetic macular edema, the patient is selected among VEGFi naïve patients, with retinal thickening in the affected eye due to diabetic macular edema.

Typically, the patient is a human patient, and more specifically an adult human patient.

Methods of Treating Inflammation Following Ocular Surgery

Efficacy has also been shown for treating of inflammation and/or pain following ocular surgery, in particular following cataract surgery (post-op cataract) with eye drop formulation of 1.5% (w/v) dexamethasone.

Hence, it is provided here a method of treating inflammation following ocular surgery, in particular following cataract surgery (post-op cataract) in a subject in need thereof, said method comprising topically administering to an affected eye of said subject, a therapeutically efficient amount of an eye drop formulation comprising 1.5% (w/v) or 3% (w/v) dexamethasone (typically a preferred formulation as described above), preferably, with a dosing of one or two drops a day, for example for a duration of at least 1-6 weeks.

In a preferred embodiment of the method, the eye drop formulation for use in the above method, comprises or essentially consists of:

1.5% of dexamethasone;
14% of γ-cyclodextrin;
2.5% of poloxamer;
0 to 0.2% of stabilizing agent, for example 0.1% of disodium edetate;
0 to 1% of electrolyte, for example 0.57% of sodium chloride;
0% to 0.6% of an additive to prevent the oxidation of the dexamethasone, for example between 0.1% and 0.5%, or between 0.2% and 0.4%, of an additive to prevent the oxidation of the corticosteroid, typically sodium thiosulfate;

and water;

wherein the % are % by weight based on the volume of the composition.

Typically, the pain and inflammation of the eyes may be significantly reduced or eliminated after 15 days of the above treatment in a patient suffering from pain and inflammation after ocular surgery, for example after cataract surgery, Pain may be determined by numerical pain rating, as described in the Examples below. Inflammation may be determined cell counts of anterior chamber cells and flare as described in the Examples below, Typically, the patient is a human patient, and more specifically an adult human patient.

Use of an Additive to Prevent Oxidation of a Corticosteroid

The present disclosure also relates to the use of an additive to prevent oxidation of a corticosteroid for stabilizing the pH of an aqueous composition comprising a corticosteroid.

EXAMPLES

Example 1: Formulation of Aqueous Dexamethasone Eye Drops

Aqueous dexamethasone eye drops having a composition according to table 1 were prepared.

TABLE 1

Aqueous dexamethasone eye drops composition

| Ingredients | Quantity (% w/v) |
| --- | --- |
| Dexamethasone | 1.50 |
| γ-cyclodextrin | 14.00 |
| Disodium edetate | 0.10 |
| Poloxamer 407 | 2.50 |
| Sodium chloride | 0.57 |
| Water for injection | q.s. 100.00 |

The eye drops were prepared as follows:

Part A: Disodium edetate, Poloxamer 407 and sodium chloride were dissolved in pure water at 80° C. The dexamethasone was added to the excipient mixture just before sterilization. Part B: γ-cyclodextrin was suspended separately in pure water at 80° C.

Part A and Part B were sterilized at 121° C. for 15 minutes. After sterilization, Part B was added to Part A at 95°

C. After stirring for 15 minutes the solution was rapidly cooled to room temperature (over 20 minutes) to form a cloudy suspension.

The suspension was then filled and sealed into glass vials or low-density polyethylene (LDPE) vials.

The pH of the eye drops in glass vials and in LDPE vials were measured during storage at 25° C. The results are shown in table 2.

TABLE 2 pH of the eye drops during storage. NT stands for not tested.

| Vial | pH at given time (months) during storage at 25° C. | | | | | | | |
|---|---|---|---|---|---|---|---|---|
| | 0 | 1 | 3 | 6 | 9 | 12 | 18 | 22 |
| LDPE vial | 4.5 | NT | 4.1 | 3.8 | 3.7 | 3.7 | 3.6 | 3.5 |
| Glass vial | NT | NT | NT | 4.36 | NT | 4.34 | NT | NT |

These results show that when the eye drops are stored in LDPE vials, the pH drops over time, while in glass vial, the pH remains stable.

Example 2: Formulation of Aqueous Dexamethasone Eye Drops Containing Sodium Thiosulfate (STS)

Eye drops with different % of sodium thiosulfate were prepared. The composition of the eye drops is shown in table 3. Sodium thiosulfate was added:

to the aqueous eye drops formulation according to table 1 (example 2A), or during the preparation of the aqueous eye drops formulation (example 2B). In this case, the eye drops were prepared according to the protocol described in example 1 and sodium thiosulfate was added in part A, together with disodium edetate, Poloxamer 407 and sodium chloride.

TABLE 3

Aqueous dexamethasone eye drops composition containing STS

| Ingredients | Quantity (% w/v) |
|---|---|
| Dexamethasone | 1.50 |
| γ-cyclodextrin | 14.00 |
| Sodium thiosulfate | 0.05 to 0.6 |
| Disodium edetate | 0.10 |
| Poloxamer 407 | 2.50 |
| Sodium chloride | 0.57 |
| Water for injection | q.s. to 100.00 |

Eye drops with 0.3% of sodium thiosulfate (corresponding to 0.471 g of sodium thiosulfate pentahydrate) and different % of dexamethasone and γ-cyclodextrin were also prepared. The compositions of the eye drops are shown in table 4 and 5. Sodium thiosulfate was added during the preparation of the aqueous eye drops formulation: the eye drops were prepared according to the protocol described in example 1 and sodium thiosulfate was added in part A, together with disodium edetate, Poloxamer 407 and sodium chloride.

TABLE 4

Aqueous 2.5% (w/v) dexamethasone eye drops composition

| Ingredients | Quantity (% w/v) |
|---|---|
| Dexamethasone | 2.50 |
| γ-cyclodextrin | 22.00 |
| Sodium thiosulfate | 0.30 |
| Disodium edetate | 0.10 |
| Poloxamer 407 | 2.50 |
| Sodium chloride | 0.57 |
| Water for injection | q.s. 100.00 |

TABLE 5

Aqueous 3.0% (w/v) dexamethasone eye drops composition

| Ingredients | Quantity (% w/v) |
|---|---|
| Dexamethasone | 3.00 |
| γ-cyclodextrin | 25.00 |
| Sodium thiosulfate | 0.30 |
| Disodium edetate | 0.10 |
| Poloxamer 407 | 3.0 |
| Sodium chloride | 0.57 |
| Water for injection | q.s. 100.00 |

Example 3: Stability Study of Aqueous Dexamethasone Eye Drops Containing STS

1. Stress Test with Oxygen and Heat

The pH of the eye drops formulations containing STS were measured after stress testing with oxygen and heat. The eye drops of examples 2A and 2B were transferred into 10 ml glass vials, where they were either purged with nitrogen or oxygen, or stored with atmosphere. All vials were placed in an autoclave and run for 0 to 4 heating cycles (each heating cycle: 121° C. for 20 min). pH was measured for all the vials after each cycle, the results are presented in tables 6 (example 2A) and 7 (example 2B).

TABLE 6 pH of eye drops formulations with various concentration of sodium thiosulfate (example 2A) after 0 to 5 cycles of autoclaving
pH of eye drops formulations containing STS

| | 0.05% STS | | 0.1% STS | |
|---|---|---|---|---|
| Cycles of autoclaving | atmosphere | purged with $O_2$ | atmosphere | purged with $O_2$ |
| 0 | 4.79 ± 0.00 | 4.79 ± 0.00 | 4.79 ± 0.02 | 4.79 ± 0.02 |
| 1 | 5.15 ± 0.07 | 4.91 ± 0.03 | 5.38 ± 0.03 | 5.52 ± 0.02 |
| 2 | 5.02 ± 0.05 | $X^a$ | 5.32 ± 0.02 | 5.15 ± 0.02 |
| 3 | 4.80 ± 0.00 | 3.92 ± 0.08 | 5.28 ± 0.03 | 4.83 ± 0.07 |
| 4 | 4.70 ± 0.00 | 3.78 ± 0.04 | 5.18 ± 0.03 | 4.52 ± 0.08 |
| 5 | | 3.65 ± 0.06[b] | | |

[a]These samples were by mistake not removed from the autoclave
[b]Since the samples were not removed from the autoclave after 2 cycles, they went for an extra cycle.

TABLE 7 pH of eye drops formulations with various concentration of sodium thiosulfate (example 2B) after 0 to 5 cycles of autoclaving. Samples were purged with oxygen prior to autoclaving.
pH of eye drops formulations with and without STS

| Cycles of autoclaving | 0% STS | 0.1%(w/v) STS | 0.2%(w/v) STS | 0.3%(w/v) STS |
|---|---|---|---|---|
| 0 | 4.78 ± 0.02 | 5.11 ± 0.01 | 5.17 | 5.26 ± 0.01 |
| 1 | 3.83 ± 0.05 | 5.82 ± 0.12 | 5.91 ± 0.02 | 5.79 ± 0.02 |
| 2 | 3.46 ± 0.03 | 5.16 ± 0.37 | 5.83 ± 0.02 | 5.77 ± 0.06 |
| 3 | 3.29 ± 0.03 | 4.66 ± 0.65 | 5.68 ± 0.02 | 5.54 ± 0.09 |
| 4 | 3.23 ± 0.02 | 3.75 ± 0.06 | 5.43 ± 0.02 | 5.49 ± 0.09 |
| 5 | — | 3.39 ± 0.03 | 5.21 ± 0.03 | 5.25 ± 0.04 |

These results show that the addition of an antioxidant, STS, prevents the pH drop of the eye drops formulation. The eye drops formulations are therefore more stable.

2. Measure of the pH Over 12 Months

The pH of the eye drops formulations containing 0.3% STS (example 2B), filled into LDPE vials and put into sealed aluminium pouches that contain air or oxygen, was also measured for 12 months at controlled temperature and humidity according to ICH guidelines (25° C./40% RH and 40° C./NMT25% RH). The results are presented in table 8.

TABLE 8 pH of eye drops formulation containing 0.3% STS.
pH of eye drops formulation with 0.3% STS - in LDPE

| Batch: OC118B-- 180410-2 | T0 | T/1 week | T 1 month | T 3 months | T 6 months | T 9 months |
|---|---|---|---|---|---|---|
| 25° C./40% RH | 5.24 | | | | | |
| Air | | NT | 5.19 | 5.28 | 5.14 | 5.27 |
| Oxygen | | NT | 5.21 | 5.27 | 5.18 | 5.27 |
| 40° C./25% RH | | | | | | |
| Air | | 5.27 | 5.26 | 5.29 | 5.18 | NT |
| Oxygen | | 5.23 | 5.31 | 5.22 | 5.05 | NT |

These studies show that the addition of an antioxidant, STS, prevents the pH drop of the eye drops formulation. The eye drops formulations are therefore stable for at least 6 months.

Example 4: Formulation of Aqueous Dexamethasone Eye Drops Containing Phenolic Antioxidants 0.02% of butylated hydroxyanisole (BHA) or butylated hydroxytoluene (BHT) were added to the aqueous eye drops formulation according to table 1.

0.005 g of BHA was dissolved in 10 µL of ethanol prior to addition to the formulation to achieve a concentration of 0.02% (w/v). 0.005 g of BHT was dissolved in 50 µL of ethanol prior to addition to the formulation to achieve a concentration of 0.02% (w/v).

The eye drops were transferred into 10 ml glass vials, where they were either purged with nitrogen or oxygen, or stored with atmosphere. All vials were placed in an autoclave and run for 0 to 3 heating cycles (each heating cycle: 121° C. for 20 min). pH was measured for all the vials after each cycle, the results are presented in table 9.

TABLE 9 pH of eye drops formulations with 0.02% of BHA or BHT after 0 to 3 cycles of autoclaving
pH of eye drops formulations with and without phenolic oxidant

| Cycles of autoclaving | 0% | 0.02% BHA | 0.02% BHT |
|---|---|---|---|
| 0 | 4.78 ± 0.02 | 4.87 | 4.87 |
| 1 | 3.83 ± 0.05 | 4.77 ± 0.08 | 4.74 ± 0.04 |
| 2 | 3.46 ± 0.03 | 4.49 ± 0.05 | 4.43 ± 0.03 |
| 3 | 3.29 ± 0.03 | 4.35 ± 0.06 | 4.20 ± 0.04 |

These results show that the addition of a phenolic antioxidant prevents the pH drop of the eye drops formulation. The eye drops formulations are therefore more stable.

Example 5: Clinical Studies Using the Eye Drops Formulations of the Present Disclosure (with 1.5% w/v Dexamethasone)

Abbreviations

AC: anterior chamber
AE: adverse events
ANCOVA: analysis of covariance
BCVA: best corrected visual acuity
BID: twice a day (from the Latin "bis in die")
CMT: central macular thickness
ETDRS: Early Treatment of Diabetic Retinopathy Study
HbA1c: hemoglobin A1c
IOP: intraocular pressure
Log MAR: logarithm of the minimum angle of resolution
QD: once a day (from the Latin "quaque die")
SD-OCT: Spectral Domain Optical Coherence Tomography
TEAEs: treatment emergent adverse events
USP: United States Pharmacopeia Grading and Measurement Scales and Methods
Anterior Chamber Cells and Flare The anterior chamber cell count is recorded as the actual number of cells observed if <10 cells are seen (only white blood cells should be counted; red blood cells and pigment cells should not be counted). (Jabs, D. A., R. B. Nussenblatt, J. T. Rosenbaum and G. Standardization of Uveitis Nomenclature Working (2005). "Standardization of uveitis nomenclature for reporting clinical data. Results of the First International Workshop." Am J Ophthalmol 140(3): 509-516) Table 10:

| Anterior Chamber Cells | | Anterior Chamber Flare | |
|---|---|---|---|
| Grade | Cell Count | Grade | Flare Count |
| 0 | 0 | 0 | None |
| 1 | 1-10 | 1 | Faint |
| 2 | 11-25 | 2 | Moderate (iris and lens details clear) |
| 3 | 26-50 | 3 | Marked (iris and lens details hazy) |
| 4 | >50 | 4 | Intense (fibrin or plasmoid aqueous) |

Scale based on (Jabs, Nussenblatt et al. 2005).

Ocular Pain

Ocular pain is assessed by the patient utilizing a numerical pain rating scale graded from 0 to 10 (McCaffery, M. and A. Beebe (1994). "Pain: clinical manual for nursing practice." Nurs Stand 9(11): 55)

The examiner asks the patient the following question:

On a scale of 0 to 10, in which 0 is no pain and 10 is the worst possible or unbearable pain, please mark on the scale the number that best describes the pain or discomfort you are feeling in the operated* eye at this time. The middle of the scale (around 5) can be used to describe "moderate pain". Only whole number scores are allowed.

Clinical Study 1: Use of Aqueous Pharmaceutical Formulation of Dexamethasone (1.5% w/v) in the Treatment of Diabetic Macular Edema This was a prospective, multi-center, randomized, double-masked, parallel group, vehicle suspension-controlled study. 144 eligible subjects were randomized in a 2:1 ratio; in one arm subjects received 1 drop of an ophthalmic microsuspension including 1.5% (w/v) of dexamethasone, 3 times a day (every 8 hours) for 12 weeks (99 subjects) and in the other arm subjects received vehicle eye drops 3 times a day (every 8 hours) for 12 weeks (45 subjects). The primary efficacy endpoint was mean change in early treatment of diabetic retinopathy study (ETDRS) BCVA at Week 12 compared to baseline. Secondary endpoints included mean change in central macular thickness (CMT) as assessed by Spectral Domain Optical Coherence Tomography (SD-OCT) at Weeks 2, 4, 8, 12, and 16 compared to baseline. Safety endpoints included AEs, safety laboratory tests, slit lamp examination parameters indicating ocular toxicity to the investigational drug, intraocular pressure, and dilated indirect ophthalmoscopy.

Efficacy Results

Best Corrected Visual Acuity

At Week 12, mean change from baseline in ETDRS BCVA letter score was higher in the tested arm with the eye drop formulation of the disclosure than in the vehicle arm; 2.9 (70% CI: 2.13, 3.65) versus 1.7 (70% CI: 0.66, 2.72). The ANCOVA results proved the alternative hypothesis and established the superiority of the eye drop formulation containing dexamethasone according to the present disclosure over Vehicle eye drop at alpha of 0.15.

Central Macular Thickness

A greater reduction in the mean CMT from baseline was observed in the tested arm with the eye drop formulation of the disclosure compared to the Vehicle arm until Week 12.

From Week 2 through Week 12, a statistically highly significant LS mean difference from baseline in the study eye CMT reduction was observed favouring tested arm; LS mean difference at Week 12; −36.77 (70% CI: −53.58, −19.95), p-value=0.01.

The results of baseline adjusted ANCOVA with multiple imputation also showed superiority of the eye drop formulation over Vehicle group for improving CMT at Week 12 (at alpha of 0.15).

Safety Results

Treatment emergent AEs were reported in a higher proportion of subjects in the group receiving the dexamethasone ophthalmic microsuspension than subjects in the Vehicle group (70 [70.0%] subjects experienced 134 TEAEs versus 24 [53.3%] subjects experienced 50 TEAEs). Serious TEAEs were reported in a higher proportion of subjects in the group dexamethasone ophthalmic microsuspension than subjects in the Vehicle group (11 [11.1%] subjects experienced 14 serious TEAEs versus 1 [2.2%] subject experienced 1 TEAE). In both treatment groups these serious TEAEs were not related to the study medication.

Clinical Study 2: Use of Aqueous Pharmaceutical Formulation of Dexamethasone (1.5% w/v) in the Treatment of Pain and Inflammation Following Cataract Surgery This was a multi-center, randomized, double-masked, placebo (vehicle)-controlled study, designed to evaluate the efficacy and safety of the eye drop formulation as disclosed in the present disclosure (with 1.5% w/v of dexamethasone) compared to placebo in treating inflammation and pain following cataract surgery.

Subjects were randomized 1:1:1 to receive the eye drop formulation with dexamethasone QD (once a day) and placebo QD, BID (twice a day), or placebo BID. Subjects dosed 1 drop in the study eye BID for 14 days, beginning one day post-surgery in the operated eye. The hierarchical primary efficacy measures were 1) absence of anterior chamber cells (i.e. score of '0') at Visit 6 (Day 15) and 2) absence of pain (i.e. score of '0') at Visit 4 (Day 4). Safety measures included changes from baseline of pin-hole VA (without any other correction) as measured on the ETDRS chart, change from baseline of IOP, and adverse event (AE) rates.

Efficacy Results

At Visit 6 (Day 15), the number of anterior chamber cells absent was significantly higher for QD (26 subjects with AC cells absent [51.0%], p=0.0009) and BID (34 subjects with AC cells absent [66.7%], p<0.0001) compared to placebo (10 subjects with AC cells absent [19.6%]). At Visit 4, the number of subjects with absence of pain was significantly higher for QD (37 subjects [72.5%], p=0.0049) and BID (32 subjects [62.7%], p=0.0738) compared to placebo (23 subjects [45.1%]).

Taken together, the primary efficacy endpoint was achieved, and results indicate that dosing with either QD or BID is significantly superior to placebo in reducing the number of subjects with anterior chamber cells and the number of subjects with pain following cataract surgery.

Safety Results

Overall, a higher proportion of TEAEs, including ocular TEAEs, were reported for the placebo group compared to either tested group. Results indicate the eye drop formulation with dexamethasone as tested is safe and well tolerated.

Example 6: Screening Studies for Use of Alternative Antioxidants

For the purpose of the present study, a set of test formulations containing different amounts of antioxidants was made. The test formulations were prepared by adding certain antioxidant as listed Table XX into the formulation as described in Table 1 of Example 1.

The concentration of antioxidants was fixed as equimolar to 0.3% w/v sodium thiosulfate. Prepared test formulations were adjusted to pH 5 (4.9-5.1) and autoclaved twice under ambient air (without oxygen inserting). After second autoclaving cycles the pH of samples were measured. The information about used antioxidants, their concentrations and results of pH measurements are presented in Table 11.

TABLE 11

Results of pH drop after 2x autoclaving cycles

| | | | pH | |
|---|---|---|---|---|
| Label | Antioxidant | Concentration used (w/v %) | Initial | After 2x autoclaving cycles* |
| Ref | Formulation without antioxidant | NA | 4.94 | 4.00 |
| SA | (+)-Sodium L-ascorbate | 0.38% | 5.06 | 4.81 |
| Cys | Cysteine | 0.23% | 4.98 | 3.86 |
| LA | Lactic acid | 0.17% | 4.96 | 4.34 |
| AP | L-Ascorbyl palmitate | 0.79%** | 5.06 | 3.58 |

TABLE 11-continued

Results of pH drop after 2x autoclaving cycles

| Label | Antioxidant | Concentration used (w/v %) | Initial pH | After 2x autoclaving cycles* |
|---|---|---|---|---|
| SFS | Sodium formaldehydesulfoxylate | 0.22% | 5.01 | 3.62 |
| LG | Lauryl gallate | 0.64%** | 5.04 | 4.54 |
| Met | L-Methionine | 0.28% | 4.95 | 5.32 |
| TBHQ | tert-Butylhydroquinone | 0.32%** | 5.06 | 4.27 |
| TA | DL-Tartaric acid | 0.28% | 5.04 | 4.74 |
| MA | DL-Malic acid | 0.24% | 4.96 | 4.83 |
| MTG | α-Monothioglycerol | 0.21% | 5.08 | 4.66 |
| SC | Sodium Citrate tribasic dihydrate | 0.48% | 5.05 | 4.95 |
| STS | Sodium thiosulfate pentahydrate | 0.30% | 5.08 | 5.56 |
| BHA | Butylated hydroxyanisole | 0.34%** | 4.92 | 4.49 |
| PCA | 3,4-dihydroxybenzoic acid | 0.29% | 4.99 | 4.97 |

*averaged of 2 measurements;
**were not dissolved completely

Considered antioxidants can be divided in several groups based on their efficiency to stabilize the formulation (see Table 12).

TABLE 12

Ranking of considered antioxidant based on their efficiency

| Group | pH drop range (abs) | Representatives |
|---|---|---|
| A | ≥0 | Sodium thiosulfate, L-Methionine, 3,4-dihydroxybenzoic acid |
| B | 0-0.5 | Sodium Citrate tribasic, DL-Malic acid, (+)-Sodium L-ascorbate, DL-Tartaric acid, α-Monothioglycerol, Butylated hydroxyanisole |
| C | 0.5-1.0 | Lauryl gallate, Lactic acid, tert-Butylhydroquinone |
| D | 1.0-1.5 | Cysteine, Sodium formaldehydesulfoxylate, L-Ascorbyl palmitate |

Antioxidants from group A, B and C showed positive effect on pH stability of the formulation, whereas representatives of group D were useless.

Discussion of the Results of the Study

For facilitating the interpretation of obtained results, the stress conditions of described studies should be converted to the condition of the currently running long term stability program for an eye drop formulation. For this purpose, the values of pH drop for stock formulations stored in glass containers from the study were compared with pH drop profile for a clinical batch stored at 25° C. in LDPE plastic containers without antioxidant (STS).

We found that the results of different heating stress tests reveal the alternative antioxidants that can be used to inhibit pH drop of OCS-01 formulation during long term storage.

Antioxidants such as L-methionine, 3,4-dihydroxybenzoic acid, sodium citrate, DL-malic acid, (+)-sodium L-ascorbate, DL-tartaric acid, α-monothioglycerol, lauryl gallate, lactic acid and tert-butylhydroquinone can stabilize the formulation during at least 1 year of storage at 25° C.

Covitol® 1100 EU, butylated hydroxyanisole, butylated hydroxytoluene and sodium thiosulfate can serve as suitable antioxidants for formulation up to 2 years of storage at 25° C.

The maximum storage time at what the mentioned antioxidants will be still effective was not studied and can exceed the storage time concluded above.

As a conclusion, among the screened antioxidants, sodium thiosulfate was the best antioxidant for stabilizing the pH of dexamethasone 1.5% ophthalmic suspension.

Additional antioxidants show stabilizing profile for dexamethasone 1.5% ophthalmic suspension. They may be less effective than STS for stabilizing the pH, but they might be able to get the stability for 2 years when stored at 25° C. in plastic/LDPE container. These antioxidants include L-methionine, 3,4-dihydroxybenzoic acid, sodium citrate, DL-malic acid, (+)-sodium L-ascorbate, DL-tartaric acid, α-monothioglycerol, lauryl gallate, lactic acid and tert-butylhydroquinone, Covitol® 1100 EU (d-alpha-tocopheryl acetate), butylated hydroxyanisole (BHA), butylated hydroxytoluene (BHT).

We claim:

1. A method of treating ocular inflammation in a human subject in need thereof, the method comprising topically administering to an affected eye of the subject an aqueous ophthalmic composition from a plastic container that allows oxidation of its contents, the composition comprising:
   i) between 1% and 4% weight to volume (w/v) of dexamethasone
   ii) between 5% and 25% w/v of γ-cyclodextrin;
   iii) an anti-oxidation means for preventing the oxidation of dexamethasone in a manner that (a) maintains a pH of between 4.5 and 6 for at least 6 months when stored at 25° C. and 40% relative humidity or (b) maintains a pH of between 4.5 and 6 after being subject to 2 cycles of autoclaving, wherein each cycle of autoclaving comprises a heating cycle of 121° C. for 20 minutes in a glass vial under ambient air, and wherein the composition is adjusted to a pH of between 4.9 and 5.1 before autoclaving; and,
   iv) water;
   wherein the composition comprises a microsuspension comprising solid complexes of dexamethasone and γ-cyclodextrin.

2. The method of claim 1, wherein the solid complexes comprise microparticles with a diameter $D_{50}$ ranging from about 1 μm to 10 μm.

3. The method of claim 1, wherein the aqueous ophthalmic composition comprises an anti-oxidation means for preventing the oxidation of dexamethasone in a manner that maintains a pH of between 4.5 and 6 for at least 6 months when stored at 25° C. and 40% relative humidity.

4. The method of claim 1, wherein the aqueous ophthalmic composition comprises an anti-oxidation means for preventing the oxidation of dexamethasone in a manner that maintains a pH of between 4.5 and 6 after being subject to 2 cycles of autoclaving, wherein each cycle of autoclaving comprises a heating cycle of 121° C. for 20 minutes in a glass vial under ambient air, and wherein the composition is adjusted to a pH of between 4.9 and 5.1 before autoclaving.

5. The method of claim 1, wherein the container is made of low-density polyethylene (LDPE).

6. The method of claim 1, wherein the anti-oxidation means for preventing the oxidation of dexamethasone is an oxygen scavenger.

7. The method of claim 1, wherein the anti-oxidation means for preventing the oxidation of dexamethasone is sodium thiosulfate.

8. The method of claim 7, wherein the sodium thiosulfate is sodium thiosulfate pentahydrate.

9. The method of claim 1, wherein the anti-oxidation means for preventing the oxidation of dexamethasone is methionine.

10. The method of claim 1, wherein the anti-oxidation means for preventing the oxidation of dexamethasone is 3,4-dihydroxybenzoic acid.

11. The method of claim 1, wherein the anti-oxidation means for preventing the oxidation of dexamethasone is selected from sodium citrate, malic acid, sodium ascorbate, tartaric acid, α-monothioglycerol, and lauryl gallate.

12. The method of claim 1, wherein the aqueous ophthalmic composition further comprises between 2.2% and 2.8% w/v of a poloxamer.

13. The method of claim 12, wherein the poloxamer is poloxamer 407.

14. The method of claim 1, wherein the aqueous ophthalmic composition further comprises between 0% and 0.2% w/v of disodium edetate.

15. The method of claim 14, wherein the aqueous ophthalmic composition comprises 0.1% w/v of disodium edetate.

16. The method of claim 1, wherein the aqueous ophthalmic composition further comprises between 0% and 1% w/v of an electrolyte.

17. The method of claim 16, wherein the electrolyte is selected from the group consisting of sodium chloride and potassium chloride.

18. The method of claim 17, wherein the electrolyte is sodium chloride.

19. The method of claim 17, wherein the electrolyte is 0.57% w/v of sodium chloride.

20. The method of claim 1, wherein the aqueous ophthalmic composition comprises 1.5% w/v of dexamethasone.

21. The method of claim 1, wherein the inflammation is associated with ocular surgery.

22. The method of claim 21, wherein the ocular surgery is cataract surgery.

23. The method of claim 22, wherein the aqueous ophthalmic composition is administered as one drop a day.

24. The method of claim 22, wherein the aqueous ophthalmic composition is administered as two drops a day.

25. The method of claim 22, wherein the aqueous ophthalmic composition is administered for a period of 1 to 6 weeks.

26. The method of claim 22, wherein the aqueous ophthalmic composition is administered for 14 days.

* * * * *